US011957899B2

(12) United States Patent
Asaad et al.

(10) Patent No.: US 11,957,899 B2
(45) Date of Patent: Apr. 16, 2024

(54) COUPLED ANNULUS AND CATHETER SYSTEM FOR PLACEMENT OF BIOCOMPATIBLE BRAIN ELECTRODES AND LIKE DEVICES

(71) Applicant: Brown University, Providence, RI (US)

(72) Inventors: Wael Asaad, Westwood, MA (US); Shane Lee, Providence, RI (US); Owen Leary, Providence, RI (US); Noah Trac, Covina, CA (US); Zakir Tahiry, Providence, RI (US); Rohan Rastogi, Westford, MA (US)

(73) Assignee: Brown University, Providence, RI (US)

( * ) Notice: Subject to any disclaimer, the term of this patent is extended or adjusted under 35 U.S.C. 154(b) by 713 days.

(21) Appl. No.: 17/151,970

(22) Filed: Jan. 19, 2021

(65) Prior Publication Data

US 2021/0138235 A1    May 13, 2021

Related U.S. Application Data

(63) Continuation-in-part of application No. 16/277,667, filed on Feb. 15, 2019, now abandoned.
(Continued)

(51) Int. Cl.
*A61N 1/05*    (2006.01)
*A61M 25/01*    (2006.01)
*A61M 25/06*    (2006.01)

(52) U.S. Cl.
CPC ....... *A61N 1/0534* (2013.01); *A61M 25/0127* (2013.01); *A61M 25/0662* (2013.01);
(Continued)

(58) Field of Classification Search
CPC ............... A61N 1/0534; A61N 1/0539; A61M 25/0127; A61M 25/0662;
(Continued)

(56) References Cited

U.S. PATENT DOCUMENTS

| 4,983,168 A | 1/1991 | Moorehead |
| 5,320,602 A | 6/1994 | Karpiel |

(Continued)

FOREIGN PATENT DOCUMENTS

| EP | 0362462 A2 | 4/1990 |
| WO | 01/32257 A1 | 5/2001 |

OTHER PUBLICATIONS

Deep Brain Stimulation, Parkinson's Foundation, Nov. 17, 2015.
(Continued)

*Primary Examiner* — Tan-Uyen T Ho
*Assistant Examiner* — Osama Nemer
(74) *Attorney, Agent, or Firm* — Adler Pollock & Sheehan P.C.

(57) ABSTRACT

A system for placement of biocompatible electrodes in an opening formed in a patient's body part, such as DBS electrodes inserted into a patient's skull during surgical procedures in the brain. The system includes a coupled catheter and annulus. The catheter includes a guide tube having at least three cooperating guide elements configured to releasably fit together and collectively form a continuous lumen through the catheter that is dimensioned to receive an electrode therein. The annulus is configured to be placed in the opening formed in the patient's body part, and to receive the catheter therethrough. A track mechanism is used to operably couple the catheter to the annulus.

18 Claims, 16 Drawing Sheets

Related U.S. Application Data

(60) Provisional application No. 62/657,454, filed on Apr. 13, 2018, provisional application No. 62/631,256, filed on Feb. 15, 2018.

(52) U.S. Cl.
    CPC ............ *A61M 2205/054* (2013.01); *A61M 2210/0693* (2013.01)

(58) Field of Classification Search
    CPC .... A61M 2205/054; A61M 2210/0693; A61B 2017/3407; A61B 2017/3409; A61B 2017/3411; A61B 2090/103; A61B 90/11; A61B 17/3468; A61B 19/201; A61B 19/20; A61B 17/3403
    See application file for complete search history.

(56) References Cited

U.S. PATENT DOCUMENTS

| | | | |
|---|---|---|---|
| RE36,857 E | 9/2000 | Euteneuer et al. | |
| 6,494,860 B2 * | 12/2002 | Rocamora | A61M 25/0668 604/161 |
| 6,544,270 B1 | 4/2003 | Zhang | |
| 6,582,390 B1 | 6/2003 | Sanderson | |
| 6,749,600 B1 * | 6/2004 | Levy | A61M 25/0668 604/324 |
| 6,920,359 B2 | 7/2005 | Meadows et al. | |
| 6,939,327 B2 | 9/2005 | Hall et al. | |
| 7,117,039 B2 | 10/2006 | Manning et al. | |
| 7,244,150 B1 * | 7/2007 | Brase | A61N 1/0551 607/46 |
| 7,682,319 B2 * | 3/2010 | Martin | A61B 18/1492 604/165.01 |
| 7,697,996 B2 | 4/2010 | Manning et al. | |
| 7,762,995 B2 | 7/2010 | Eversull et al. | |
| 7,857,820 B2 | 12/2010 | Skakoon et al. | |
| 7,985,232 B2 * | 7/2011 | Potter | A61B 17/3421 606/129 |
| 9,180,299 B2 | 11/2015 | Decre et al. | |
| 9,474,894 B2 | 10/2016 | Mercanzini et al. | |
| 10,856,981 B2 * | 12/2020 | Maimon | A61F 2/2436 |
| 11,565,093 B2 * | 1/2023 | Kirt | A61M 25/0662 |
| 2006/0041230 A1 | 2/2006 | Davis | |
| 2009/0259272 A1 | 10/2009 | Reddy et al. | |
| 2010/0010449 A1 | 1/2010 | Leibowitz et al. | |
| 2011/0137372 A1 | 6/2011 | Makous et al. | |
| 2011/0230893 A1 * | 9/2011 | Barker | A61N 1/0551 607/148 |
| 2012/0010627 A1 * | 1/2012 | Watschke | A61B 17/3468 606/129 |
| 2013/0053867 A1 * | 2/2013 | Gowda | A61B 90/11 606/130 |
| 2014/0350635 A1 | 11/2014 | Strother et al. | |
| 2017/0202631 A1 * | 7/2017 | Piferi | A61B 90/11 |

OTHER PUBLICATIONS

"Lead kit for deep brain stimulation", Minneapolis MN: Medtronic, 2002.

Ashkan et al., "Insights Into the Mechanisms of Deep Brain Stimulation", Nature Rev Neurology, vol. 13, Issue 9, 2017, pp. 548-554.

Butson et al., "Sources and Effects of Electrode Impedance During Deep Brain Stimulation", Clinical Neurophys, vol. 117. Issue 2, 2006, pp. 447-454.

Hickey et al., "Deep Brain Stimulation: a Paradigm Shifting Approach to Treat Parkinson's Disease", Frontiers in Neuroscience, vol. 10, Issue 173, Apr. 28, 2016, 11 pages.

Koller et al., "High Frequency Unilateral Thalamic Stimulation in the Treatment of Essential and Parkinsonian Tremor", Annals Neurology, vol. 42, Issue 3, 1997, pp. 292-299.

Karamintziou SD, et al. Design of a novel closed-loop deep brain stimulation system for Parkinson's disease and obsessive-compulsive disorder. Neural Engineering (2015).

Lyons, "Deep Brain Stimulation: Current and Future Clinical Applications", Mayo Clinic Proc, vol. 86, Issue7, 2011, pp. 662-672.

Mayberg et al., "Deep Brain Stimulation for Treatment-resistant Depression", Neuron, vol. 45, 2005, pp. 651-660, Mar. 3, 2005.

Mcconnell et al., "Implanted Neural Electrodes Cause Chronic, Local Inflammation That is Correlated With Local Neurodegeneration", J Neural Eng, vol. 6, Issue 5, 2009, 056003, 2 pages.

Moss et al., "Electron Microscopy of Tissue Adherent to Explanted Electrodes in Dystonia and Parkinson's Disease", Brain, vol. 127, Issue 12, 2004, pp. 2755-2763.

Rao et al., "Polyethylene Glycol-containing Polyurethane Hydrogel Coatings for Improving the Biocompatibility of Neural Electrodes", Acta Biomaterialia, vol. 8, Issue 6, 2012, pp. 2233-2242.

Steigerwald F, Volkmann J, et al. Direct DBS: A prospective, multi-center clinical study with blinding for a directional deep brain stimulation (DBS) lead (p. 4.068). Neurology (2018).

"Food and Drugs", Food and Drug Administration Department of Health and Human Services, Subchapter H—Medical Devices, Part 882—Neurological Devices, Sec. 882.5800 Cranial electrotherapy stimulator, Available at https://www.accessdata.fda.gov/scripts/cdrh/cfdocs/cfcfr/cfrsearch.cfm?FR=882.5800, vol. 8, Apr. 1, 2020, 3 pages.

Vitek J, Jain R, Starr P. INTREPID Trial: A prospective, double blinded, multi-center randomized controlled trial evaluating deep brain stimulation with a new multiple-source, constant-current rechargeable system in Parkinson's Disease (p. 5.016). Neurology (2017).

Parastarfeizabadi M, Kouzani AZ. Advances in closed-loop deep brain stimulation devices. J Neuroeng Rehabil (2017).

Johnson LA, Nebeck SD, et al. Closed-loop deep brain stimulation effects on Parkinsonian motor symptoms in a non-human primate—is beta enough? Brain Stimul (2016).

Wu H, Ghekiere H, et al. Conceptualization and validation of an open-source closed loop deep brain stimulation system in rat. Scientific Reports (2015).

Tröster A, et al. Memory and mood outcomes after anterior thalamic stimulation for refractory partial epilepsy. Seizure (2017).

Sandok E, et al. Long term outcomes of the SANTE trial: 7-year follow-up. American Epilepsy Society Annual Meeting (2016).

Widge AS, et al. Closing the loop on deep brain stimulation for treatment-resistant depression. Front Neurosci (2018).

Sapiens' Deep Brain Stimulation Technologies Strengthen Medtronic's Neuromodulation Portfolio and Neuroscience Leadership Position, Medtronic, Press Release, Aug. 26, 2014.

* cited by examiner

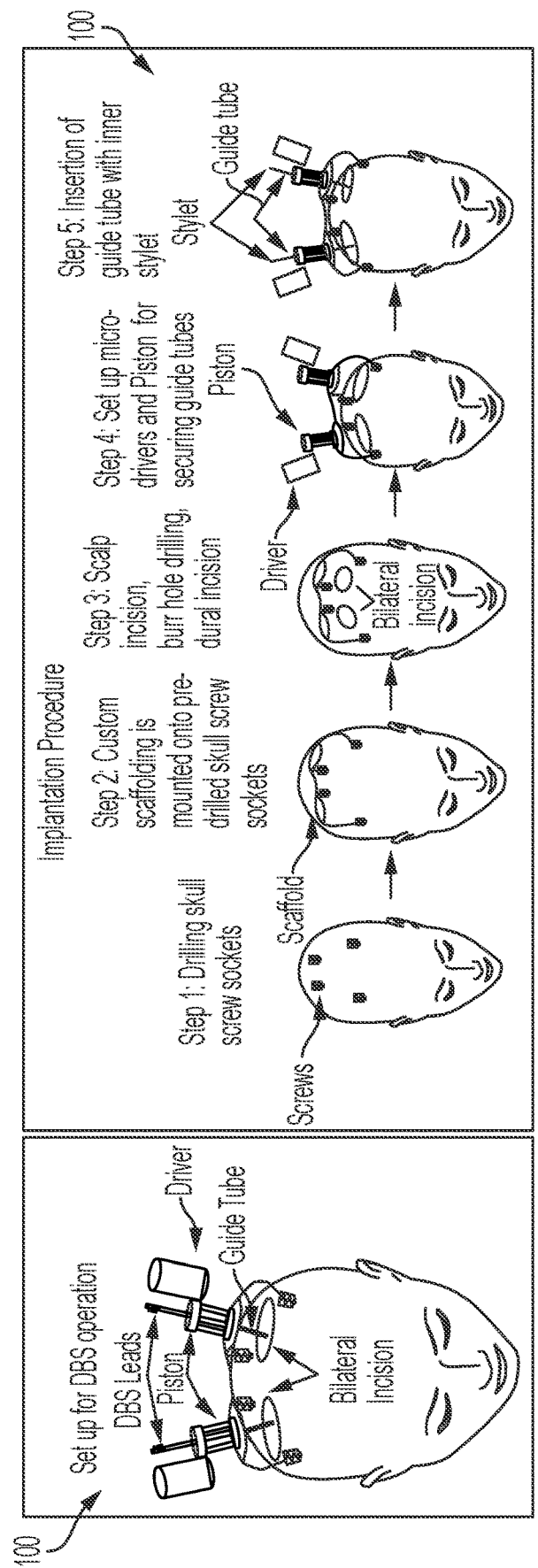
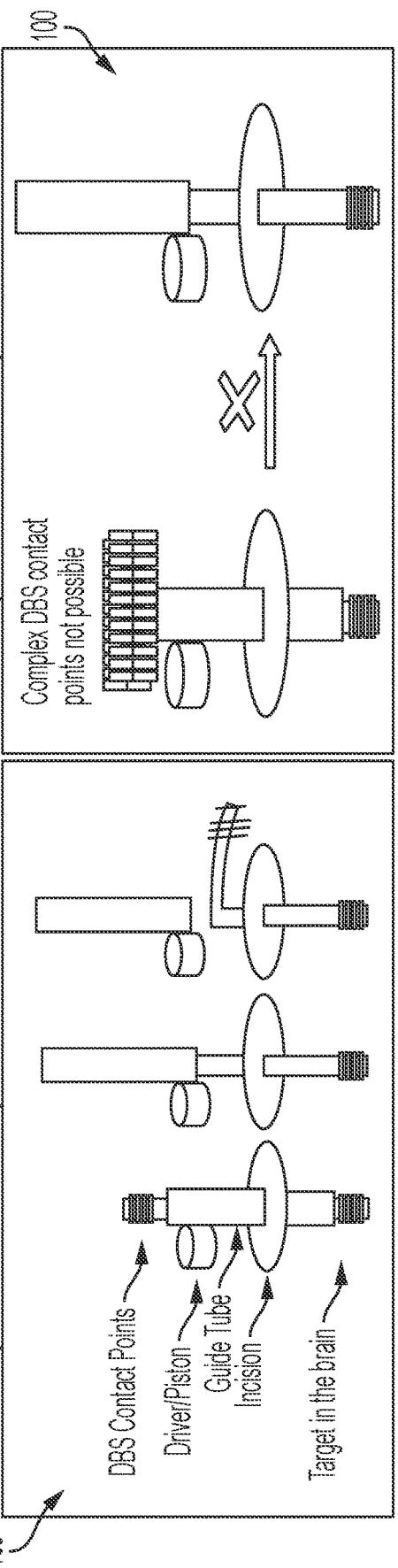
FIG. 1A (PRIOR ART)
FIG. 1B (PRIOR ART)
FIG. 1C (PRIOR ART)
FIG. 1D (PRIOR ART)

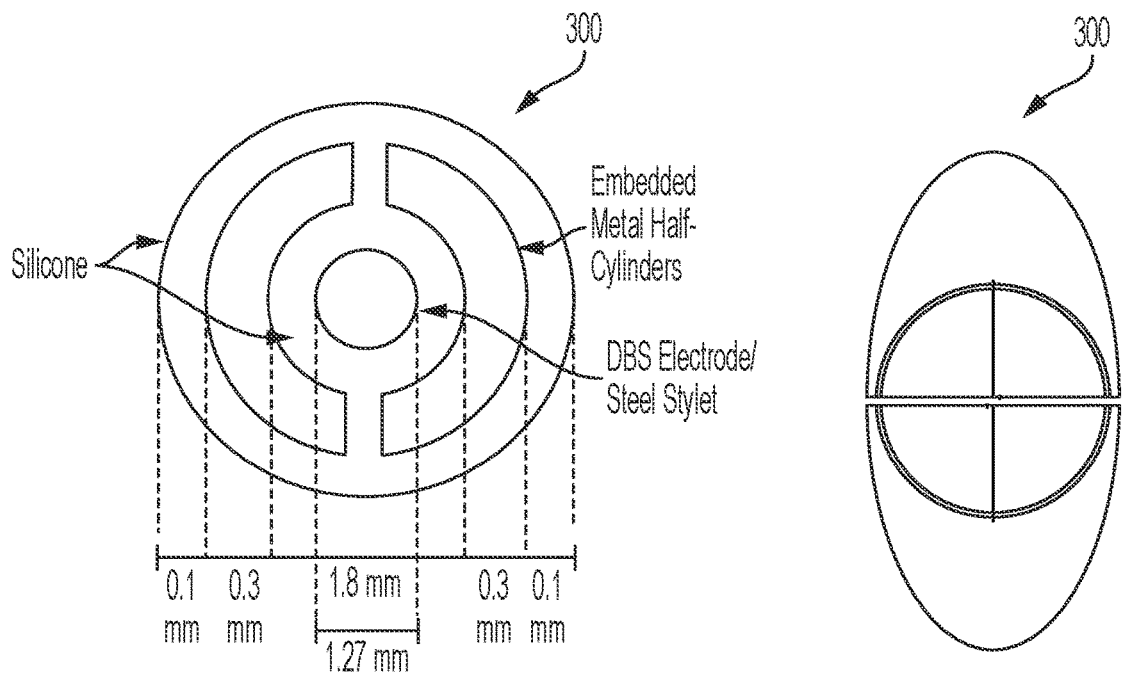
FIG. 3A
FIG. 3B
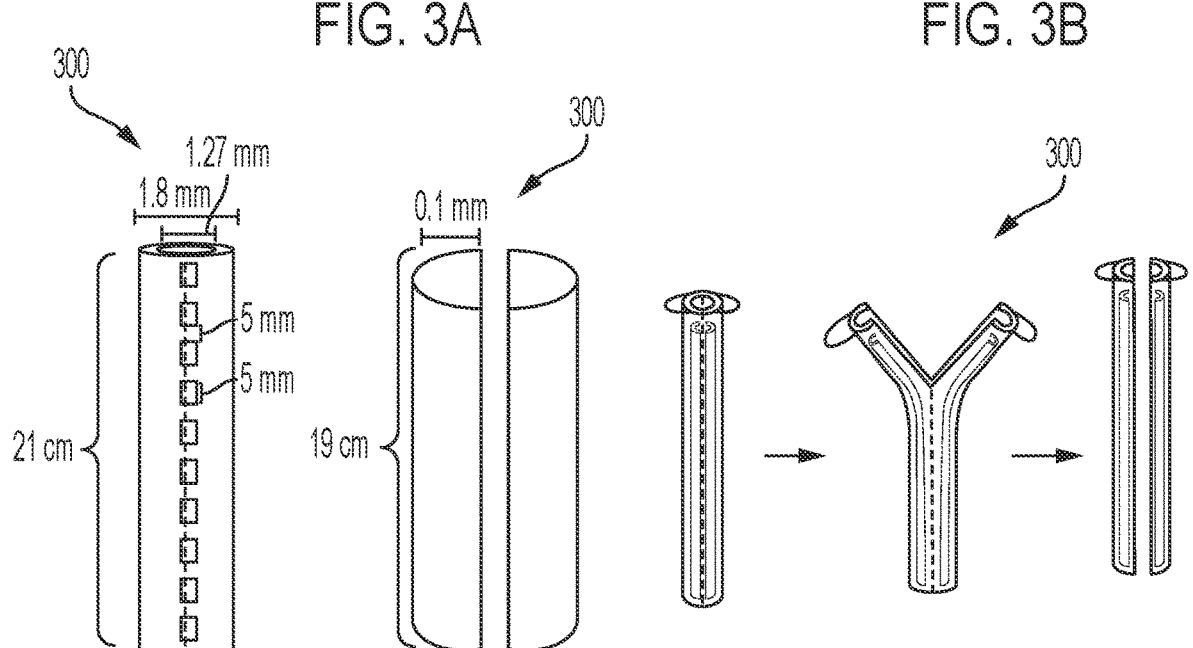
FIG. 3C
FIG. 3D
FIG. 3E

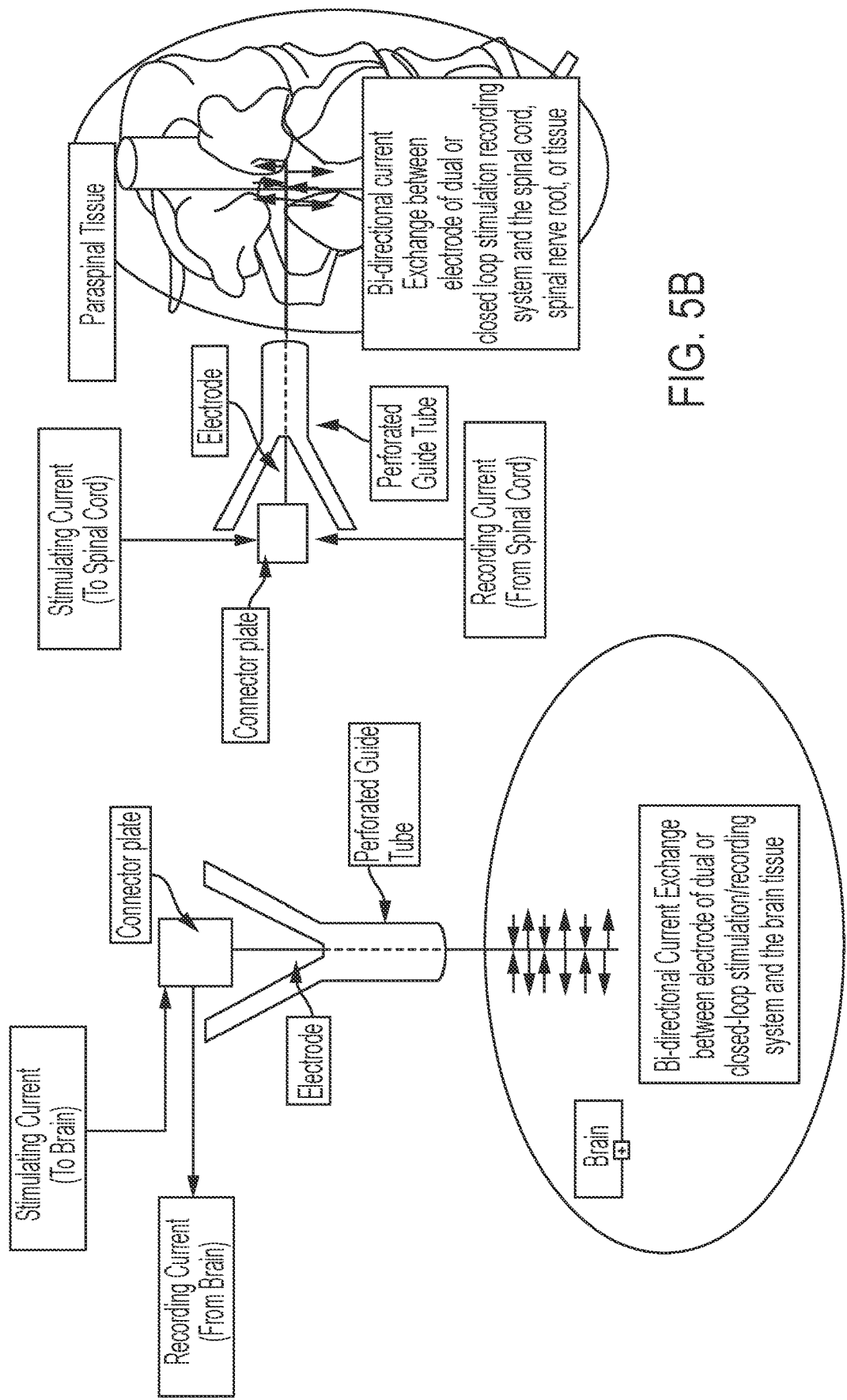

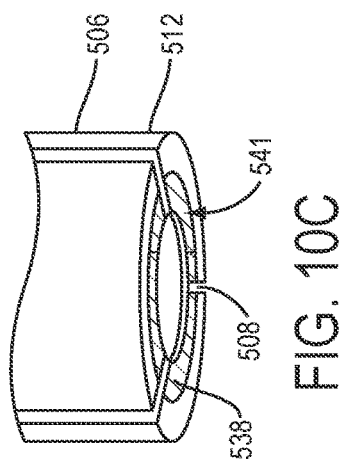
FIG. 10C
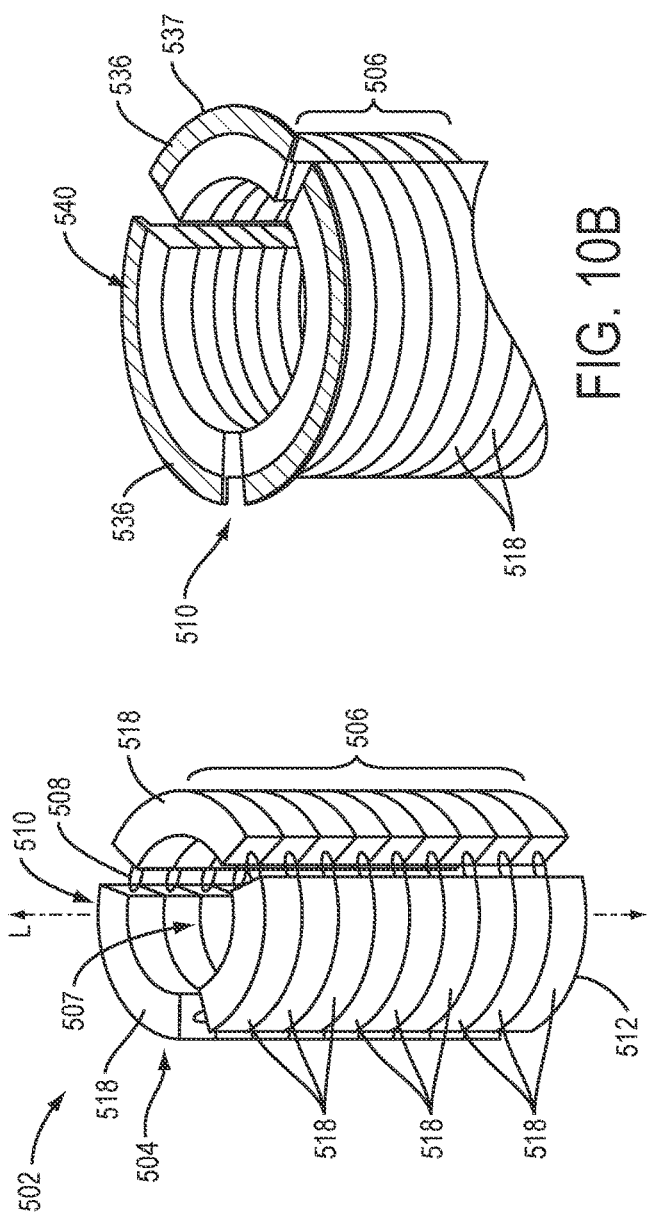
FIG. 10B
FIG. 10A
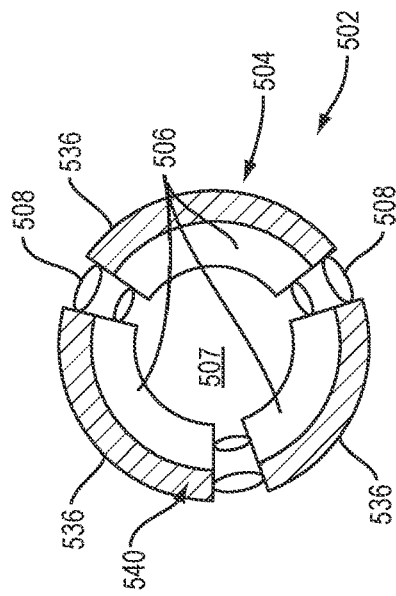
FIG. 10E
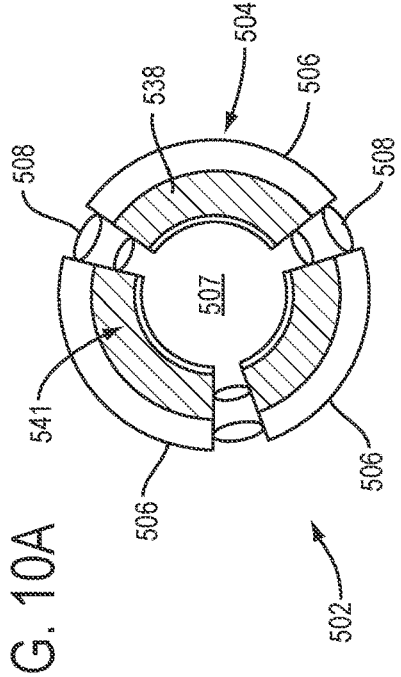
FIG. 10D

COUPLED ANNULUS AND CATHETER SYSTEM FOR PLACEMENT OF BIOCOMPATIBLE BRAIN ELECTRODES AND LIKE DEVICES

CROSS REFERENCE TO RELATED APPLICATIONS

This application is a continuation-in-part of U.S. patent application Ser. No. 16/277,667 filed Feb. 15, 2019, and claims benefit from U.S. Provisional Patent Application Ser. No. 62/631,256 filed Feb. 15, 2018, and U.S. Provisional Patent Application Ser. No. 62/657,454 filed Apr. 13, 2018, each of which said three applications are incorporated by reference in their entireties.

STATEMENT REGARDING GOVERNMENT INTEREST

None.

BACKGROUND OF THE INVENTION

This invention generally relates to catheters, and more specifically to a peel-away electrode placement catheter and related systems and methods including such a catheter.

Deep brain stimulation (DBS) of specific areas of the brain has been used with great success as a clinical treatment for a range of neurological and psychiatric disorders rooted in often Progressive abnormalities of the underlying neural circuitry, including essential tremor, schizophrenia, and Parkinson's disease. More recently DBS has been attempted with some success to treat an even wider range of neuro disorders, including epilepsy, obsessive compulsive disorder (OCD), and major depression. This treatment is increasingly common.

SUMMARY OF THE INVENTION

The following presents a simplified summary of the innovation in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

In general, in one aspect, the invention features a catheter including a silicone tube, the silicone tube including perforations longitudinally positioned to split the silicone tube in half, and a pair of separate metal semi-cylinders positioned within the silicone tube.

In another aspect, the invention features a peel-away electrode placement catheter including a silicone tube, the silicone tube including perforations longitudinally positioned to split the silicone tube in half, a pair of separate metal semi-cylinders positioned within the silicone tube, and a deep brain stimulation (DBS) implantable electrode positioned between the pair of separate metal semi-cylinders.

In another aspect, the invention features a system for placement of biocompatible electrodes in an opening formed in a patient's body part. The system comprises a catheter including a guide tube, the guide tube having a longitudinal axis and at least three guide elements extending along the longitudinal axis; each of the guide elements including a first end, a second end, a plurality of rotatably-connected segments extending between the first and second ends, and a plurality of joints connecting adjacent ones of the segments. The guide elements are configured to releasably fit together and collectively form a continuous lumen through the catheter, the lumen extending along the longitudinal axis of the guide tube and being dimensioned to receive an electrode therein. The system further comprises an annulus including a circumferential rim defining an interior circular space that is dimensioned to receive the catheter therethrough, and a number of legs engaging the rim and extending outwardly therefrom, the annulus being configured to be secured in the opening; and means for operably coupling the catheter to the annulus.

In another aspect, the invention features a system for placement of DBS electrodes in an opening formed in a patient's skull. The system comprises a catheter including a guide tube, the guide tube having a longitudinal axis and at least three guide elements extending along the longitudinal axis; each of the guide elements including first end, a second end, a plurality of rotatably-connected segments extending between the first and second ends, and a plurality of joints connecting adjacent ones of the segments, the guide elements being configured to releasably fit together and collectively form a continuous lumen through the catheter, the lumen extending along the longitudinal axis of the guide tube and being dimensioned to receive a DBS electrode therein. The catheter is moveable between a first, united cylindrical configuration with each one of the guide elements of the guide tube being fully interconnected to the others of the guide elements, and a second, separated configuration with the guide elements being at least partially disengaged from each other. The system further comprises an annulus including a circumferential rim defining an interior circular space that is dimensioned to receive the catheter therethrough and a number of legs engaging the rim and extending outwardly therefrom, the annulus being configured to be secured in the skull opening. The system further comprises a track mechanism connected to the annulus, the track mechanism including at least one toothed gear, and teeth protruding from each of the rotatably-connected segments of the guide elements and configured to operably engage teeth of the at least one gear, whereby the annulus and catheter are operably coupled to each other, whereby lateral movement of the guide elements is limited by the at least one gear, and axial movement into and out of the skull opening is carefully controlled.

In another aspect, the invention features a kit for the placement of DBS electrodes into an opening in a patient's skull. The kit comprises a catheter including a guide tube, the guide tube having a longitudinal axis and at least three guide elements extending along the longitudinal axis; each of the guide elements including first end, a second end, a plurality of rotatably-connected segments extending between the first and second ends, and joints connecting adjacent ones of the segments. The guide elements are configured to releasably fit together and collectively form a continuous lumen through the catheter, the lumen extending along the longitudinal axis of the guide tube and being dimensioned to receive a DBS electrode therein. The catheter is moveable between a first, united cylindrical configuration with each one of the guide elements of the guide tube being fully interconnected to the others of the guide elements, and a second, separated configuration with the guide elements being at least partially disengaged from each other. The kit further comprises an annulus including a circumferential rim defining an interior circular space that is dimensioned to receive the catheter therethrough and a number of legs engaging the rim and extending outwardly therefrom, the annulus being configured to be secured in the skull opening. The kit further comprises a track mechanism connected to the annulus, the track mechanism including at least one toothed gear, and teeth protruding from each of the rotatably-connected segments of the guide elements and configured to operably engage teeth of the at least one gear, whereby the annulus and catheter are operably coupled to each other; and a stylet that is configured to urge the guide elements in a distal direction for facilitating insertion of the catheter into the skull opening.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

These and other features, aspects, and advantages of the present invention will become better understood with reference to the following description, appended claims, and accompanying drawings where:

FIG. 1A, FIG. 1B, FIG. 1C and FIG. 1D illustrate an exemplary prior art design of a guide tube.

FIG. 3A, FIG. 3B, FIG. 3C, FIG. 3D and FIG. 3E illustrate an exemplary perforated peel-away catheter.

FIG. 5A and FIG. 5B illustrate different perforated peel-away catheter applications.

FIG. 10A is a schematic, perspective view of components of a catheter of an exemplary coupled annulus and catheter system according to the present invention.

FIG. 10B is a partial top perspective view of the catheter of FIG. 10A and its components.

FIG. 10C is a partial bottom perspective view of the catheter of FIG. 10A and its components.

FIG. 10D is a bottom elevational view of the catheter of FIG. 10A and its components.

FIG. 10E is a top elevational view of the catheter of FIG. 10A and its components.

DETAILED DESCRIPTION

Figure 2:
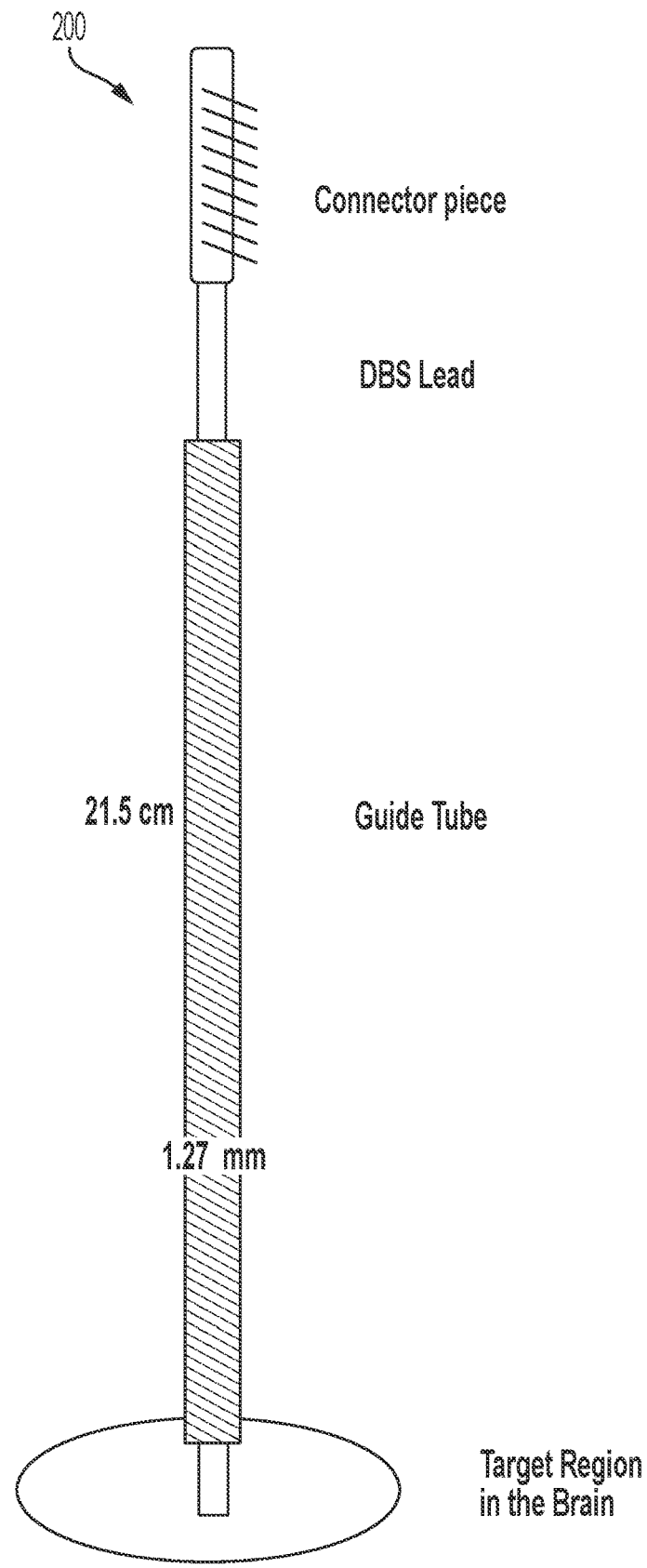
FIG. 2 illustrates a standard prior art guide tube.

The subject innovation is now described with reference to the drawings, wherein like reference numerals are used to refer to like elements throughout. In the following description, for purposes of explanation, numerous specific details are set forth in order to provide a thorough understanding of the present invention. It may be evident, however, that the present invention may be practiced without these specific details. In other instances, well-known structures and devices are shown in block diagram form in order to facilitate describing the present invention.

The standard electrode insertion catheter (herein referred to as a "guide tube") that is used to guide the implantation of DBS electrodes is a uniform, inflexible, hollow cylinder with approximate dimensions of 1.27 mm inner diameter, 1.8 mm outer diameter and 21 cm length. Flexible, delicate stimulating electrodes are guided to their deep brain targets through these thin steel guide tubes. Due to their rigid geometry, the guide tubes must then be withdrawn over the extracranially-protruding ("proximal") end of the implanted DBS electrode after the electrode has been inserted. Because the guide tube must be fully withdrawn after electrode implantation, the connection that must be established between the proximal end of the electrode and the other components of the stimulator system must therefore be established after the guide tube is withdrawn. The procedural step of withdrawing a rigid guide tube therefore limits the complexity of the electrical connections that can be established at the proximal end of the electrode, due to the lack of available connector technologies that can be swiftly assembled intraoperatively and also accommodate increased number of electrical channels embedded in the electrode. Connector setups that take significantly more time to assemble intraoperatively are not acceptable to surgeons, even for the benefit of accommodating more electrical channels, because of the increased risk of operative complication with increased surgical time. Further, this constraint limits potential improvements to the therapeutic efficiency of the procedure that might be possible with more intricate stimulating and recording electrodes that require a more complex and time-consuming connector setup (e.g., closed loop DBS). there is a clinical need to improve the surgical procedure of DBS, or the equipment used there in, to maximize the therapeutic efficiency of DBS by enhancing intraoperative testing and usage of such more powerful and complex electrode-connector systems. One goal of the present invention is to provide a guide tube that can be peeled away by the surgeon into multiple separate pieces as it is withdrawn over the electrodes which were inserted through its lumen.

By obviating the need for the guide tube to be pulled over the proximal end of the electrode, the present invention alleviates the limitations on electrode complexity imposed by the fixed guide tube geometry of current devices. A peel-away guide tube opens the possibility of manufacturing more complex electrode connector systems that accommodates a greater number of recording and stimulating channels within the electrode proper, since the peel away tube enables intraoperative implementation of such systems without need for additional assembly during the surgical procedure. In one embodiment, the design of the present invention is a longitudinally perforated peel away guide tube with the same external dimensions as the currently standard steel device. It includes deformable silicone rubber with steel semicircular inserts embedded in the silicon between the perforations. Pull tabs are featured to aid intraoperatively splitting the silicone rubber tubing along the perforations as it is withdrawn from the cranium.

The design of the present invention reimagines the uniform steel insertion catheter design typically used in DBS surgery during the electrode insertion step. Specifically, the present design includes (1) an insertion catheter for electrodes, or for other biomedical devices applied or implanted intracranially (such as neurochemical delivery systems or measurement systems) whose outer casing is made of silicone, (2) and insertion catheter for electrodes, or for other biomedical devices applied or implanted intracranially, that can split in half longitudinally along predefined preparations such that controlled deformation upon withdrawal from the brain tissue can be achieved, (3) an insertion catheter for electrodes, or for other biomedical devices applied or implanted intracranially, made of an outer silicone casing that also includes dual steel semi-cylinders embedded such that the tube retains its rigidity upon insertion into the brain tissue and until intentional tearing stresses are applied to break it along the perforations, (4) an insertion catheter for electrodes, or for other biomedical devices applied or implanted intracranially, that is readily deformable with less than 5 N force applied to opposite sides of the tube, (5) and insertion catheter that need not interrupt pre-established connections between the stimulating or recording electrode implanted through the catheter and the rest of the DBS system, or more broadly the connections between any biomedical device inserted through the catheter and its corresponding extra cranial components.

Using the design of the present invention, the ergonomics of the DBS procedure are not altered, nor additional burden is imposed on the patient or a user neurosurgeon, and all geometric and functional requirements defined by current electrode insertion catheters are met. The present design uniquely leverages and combines material properties of silicon and steel to produce the desired functional outcome. the design effectively opens a gateway to further advances in the therapeutic impact of deep brain stimulation by enabling the use of more complex, versatile stimulating and recording electrodes, towards eventual application of closed-loop DBS.

FIG. 1A, FIG. 1B, FIG. 1C and FIG. 1D illustrate an exemplary prior art design of a guide tube 100. More specifically, FIG. 1A illustrates an exemplary DBS procedural setup, FIG. 1B illustrates the exemplary steps of surgical electrode implantation, FIG. 1C illustrates exemplary steps of guide tube removal and FIG. 1D illustrates the clinical problem associated with this device and technique, i.e., an inability to withdraw the guide tube over the distal end.

In FIG. 2, a standard prior art guide tube 200 is shown and includes a hollow steel cylinder, with an inner diameter of 1.27 mm, outer diameter of 1.8 mm and a length of 21 cm. Given the rigidity of the guide tube 200, it must be withdrawn over the proximal end of the DBS lead during removal, forcing the neurosurgeon to establish the electrical connections after removal, and limiting the power and versatility of the electrical system used. A primary aim of the present invention used to develop a guide tube that alleviate such limitations, enabling the DBS lead to be manufactured with pre-established connections. Another objective is to design a guide with geometric dimensions that closely adhere to those of the currently used guide tube so as not to interfere with the current ergonomics of the insertion procedure or the size of the burr hole to be drilled in the patient's skull.

As shown in FIG. 3A, FIG. 3B, FIG. 3C, FIG. 3D and FIG. 3E, an exemplary perforated peel-away guide tube 300 includes deformable silicone rubber with steel semicylinder inserts embedded in the silicon between the perforations. the perforated peel-away guide tube 300 features approximately the same geometry and dimensions as the prior art steel guide tube. Pull tabs are added to aid in intraoperative deformation of the silicone rubber tubing.

More specifically, FIG. 3A illustrates a cross sectional perspective of the silicon and steel guide tube, FIG. 3B illustrates the pull flaps, FIG. 3C illustrates a side view of the silicone tube perforations, FIG. 3D illustrates a side view of the dual steel semi-cylinders, and FIG. 3E illustrates the combined silicone and steel components.

Figure 4:
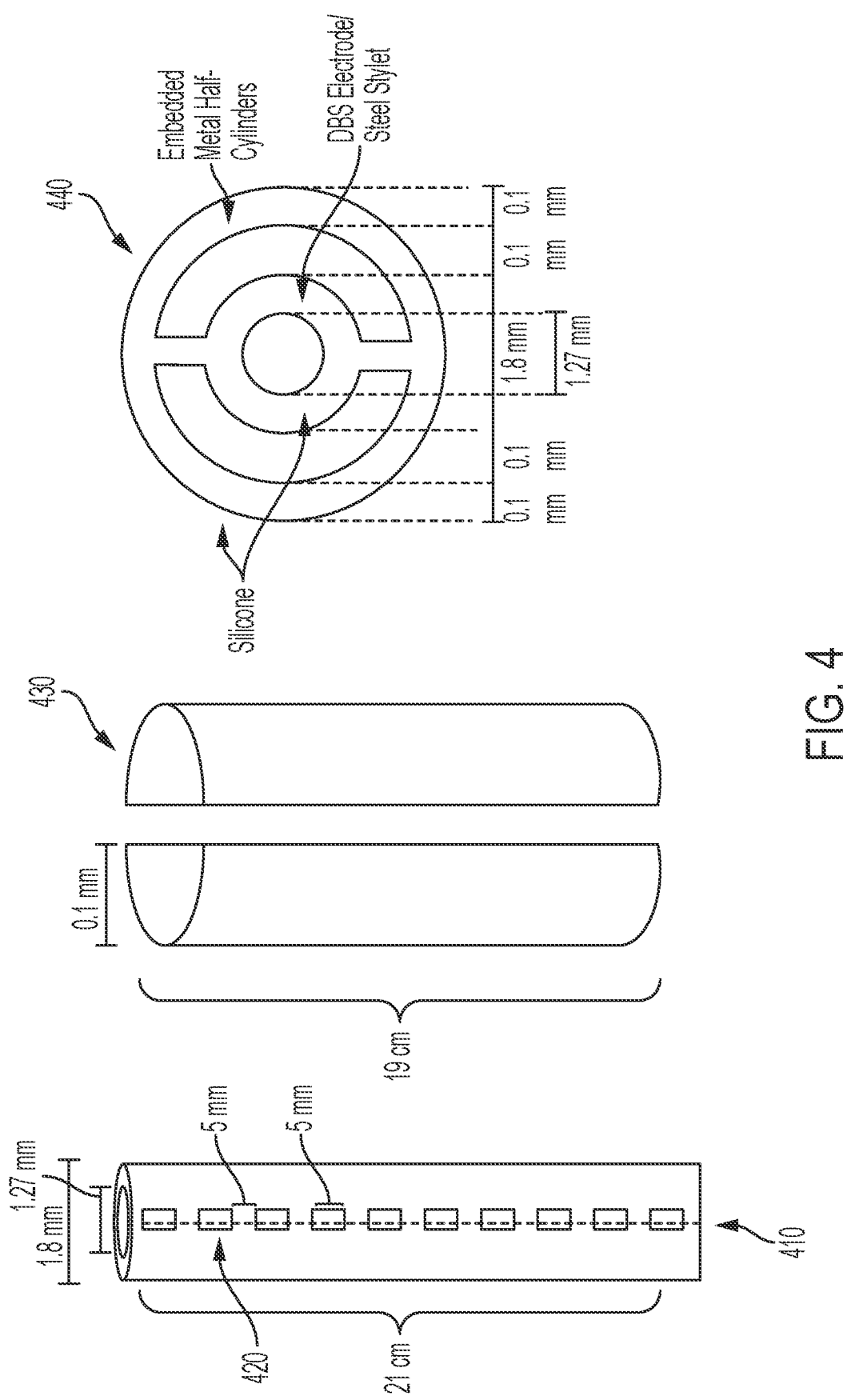
FIG. 4 illustrates exemplary design specifications of the perforated peel-away catheter.

In FIG. 4, exemplary design specifications of the perforated peel-away guide tube 300 are shown. The silicone tube 410 includes an inner diameter of about 1.27 mm, an outer diameter of about 1.8 mm and an over length of about 21 cm. Perforations 420 are spaced equally 5 mm apart. The metal semi-cylinder 430 is about 19 cm in length. In the top view 440, exemplary dimensions of the silicone, embedded metal semi-cylinders and DBS electrode/steel stylet are shown.

Figure 6B:
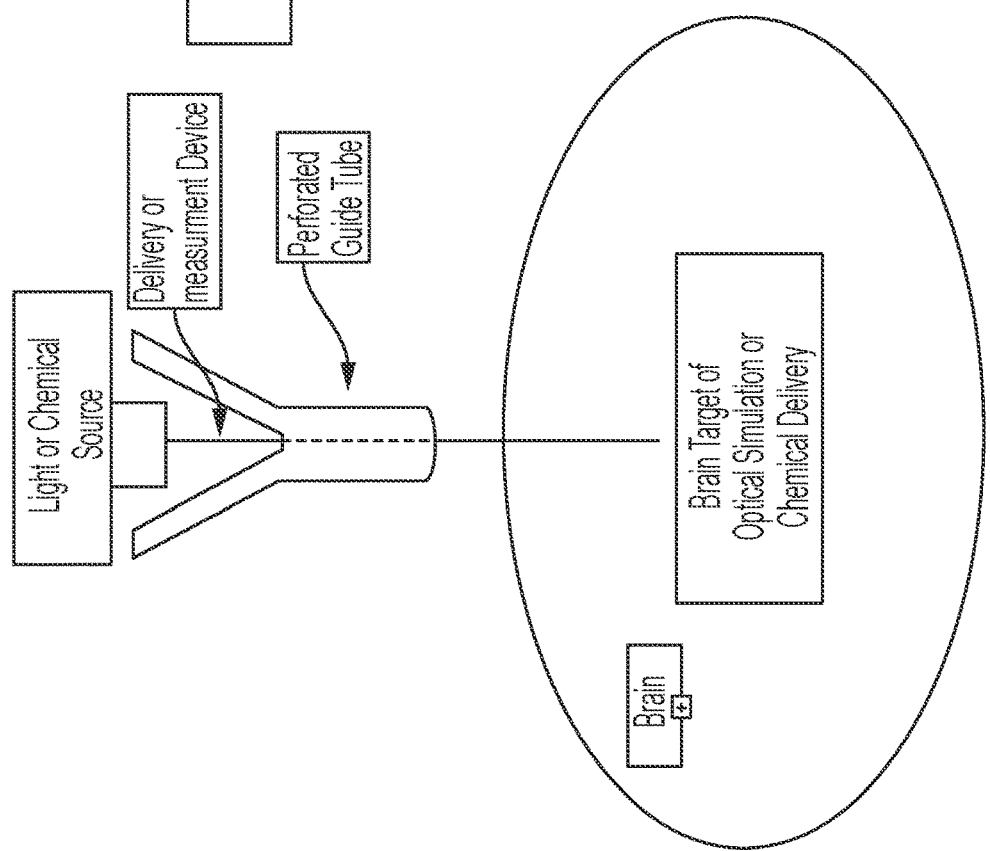
FIG. 6A and FIG. 6B illustrate additional perforated peel-away catheter applications.
Figure 6A:
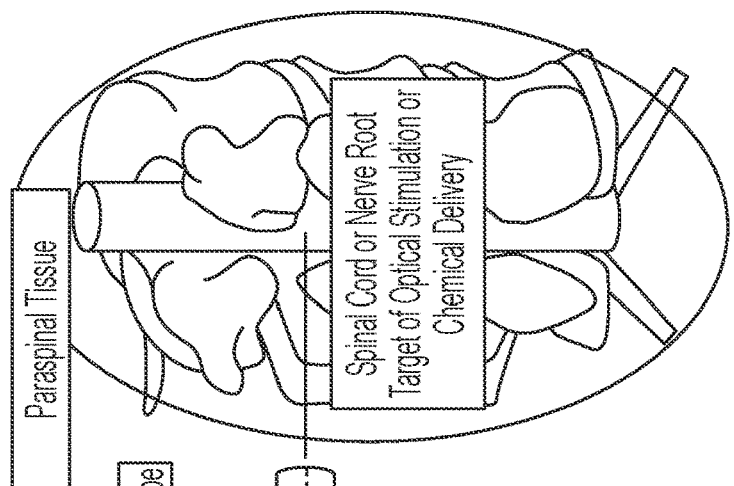

The perforated peel-away guide tube 300 may additionally be implanted intraspinally, and the potential usages for either brain or spine include, but are not limited to, implantation of stimulating electrodes, recording electrodes, electrodes that operate to both record and stimulate simultaneously or distinctly (see FIG. 5A and FIG. 5B), optical recording and stimulation (e.g., optical coherence tomography systems, OCT), and chemical assay and delivery systems (e.g. intrathecal pain medication, neurotransmitter delivery systems, amperometry or voltometry systems) (see FIG. 6A and FIG. 6B). For all of these potential usages, our catheter can be used for devices intended to be implanted either permanently or temporarily. In spinal applications, the device may enable interaction with either the spinal cord proper, or with any of the spinal nerve roots, rootlets, or cauda equina. Furthermore, the device's technical dimensions and specifications as described elsewhere in these application documents may be optimized for use in any of these applications, with potential modifications including but not limited to alterations in internal or external diameter, wall thickness, spacing of metal hemi-cylindrical inserts within the flexible wall, specific grade of materials used for metal or silicone components, and/or including either a closed or open end to the catheter.

Importantly, the perforated peel-away guide tube 300 may be used for many applications not traditionally defined as, nor necessarily related to, DBS, though DBS is one particularly impactful application for which it might be used therapeutically in the short term.

In other embodiments, the perforated peel-away guide tube 300 may include, as a connected or separate component, a cylindrical annulus made of any biocompatible material, including certain plastics or metals, with one or multiple bores each no less than the size of the peel away catheter, with one or multiple hinges that open around the bores, and with eyelets for affixing the cylindrical annulus to the skull. Biocompatible skull screws can be separate or pre-attached and securely but freely spinning in the eyelets. One purpose of the annulus is to discourage peeling of the catheter beneath the cylinder, and to enable one or multiple catheters to be inserted and safely removed above the annulus without inflicting damage on cortical or subcortical tissues.

Figure 7:
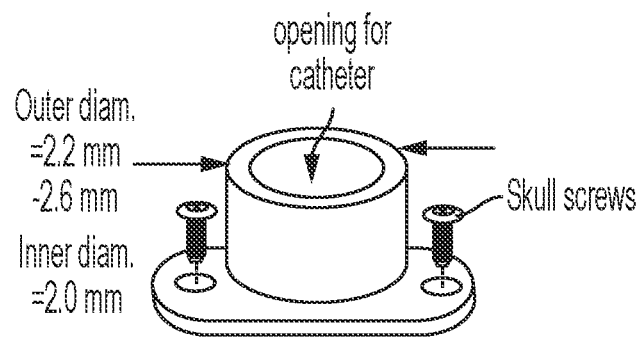
FIG. 7 illustrates an exemplary annulus.

In FIG. 7, an exemplary annulus is constructed of biocompatible material, such as steel with one bore to accommodate passage of a 1.8 mm peel-away catheter and peripheral holes (×2) for fixation to the intraoperatively exposed skull via biocompatible skull screws. A base plate features holes to accommodate the skull screws.

Figure 8A:
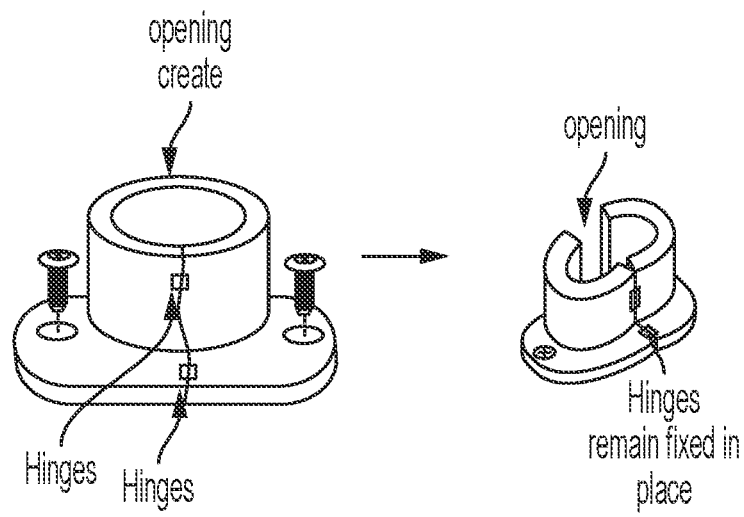
FIG. 8A and FIG. 8B illustrate another exemplary annulus.
Figure 8B:
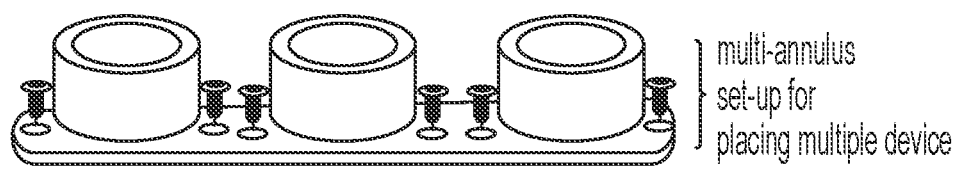

In FIG. 8A and FIG. 8B, the cylindrical annulus design may be modified to accommodate new constraints imposed by a peel-away catheter and the application involved. In FIG. 8A, hinges are implemented to enable easier placement and removal of the annulus after the catheter itself has already been placed, such that the annulus can provide additional as the catheter is peeled. In FIG. 8B, as many trajectories are tested before one is selected for permanent DBS implant via separate electrodes, a multi-annulus array is designed to enable this. Moreover, the base plate may be curved to accommodate anatomical curvature of the cranium.

FIGS. 9-17 illustrate a system 500 for placement of biocompatible electrodes (e.g., DBS electrodes and like devices) in a patient's body part (e.g., the patient's skull) and components of the system according to exemplary embodiments of the present invention. As described below, the system includes coupled, cooperating catheter and annulus components.

Figure 14:
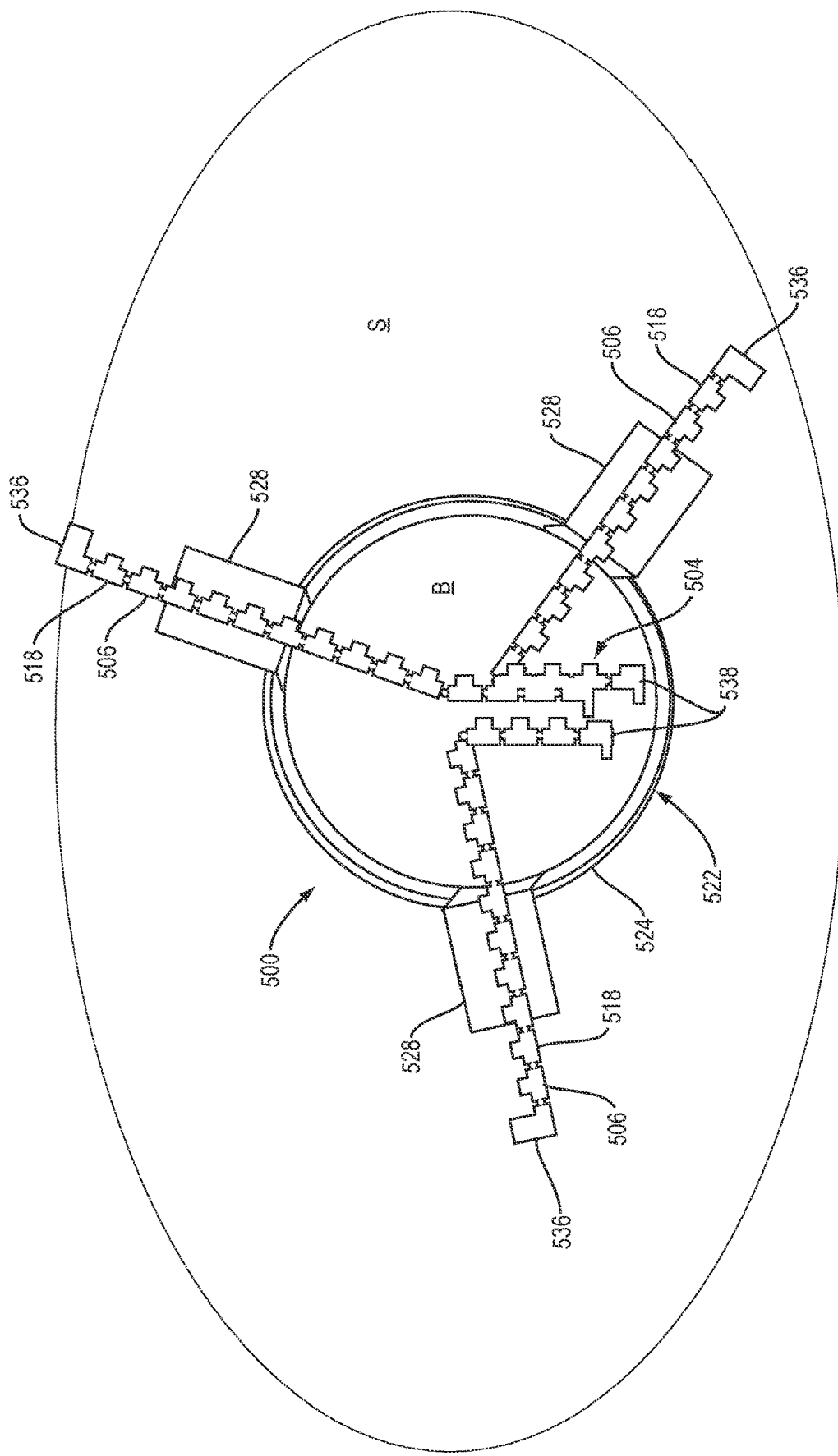
FIG. 14 is an environmental, schematic view of an exemplary coupled annulus and catheter system for placement of biocompatible electrodes and like devices according to the present invention, as used in a patient's skull.
Figure 15:
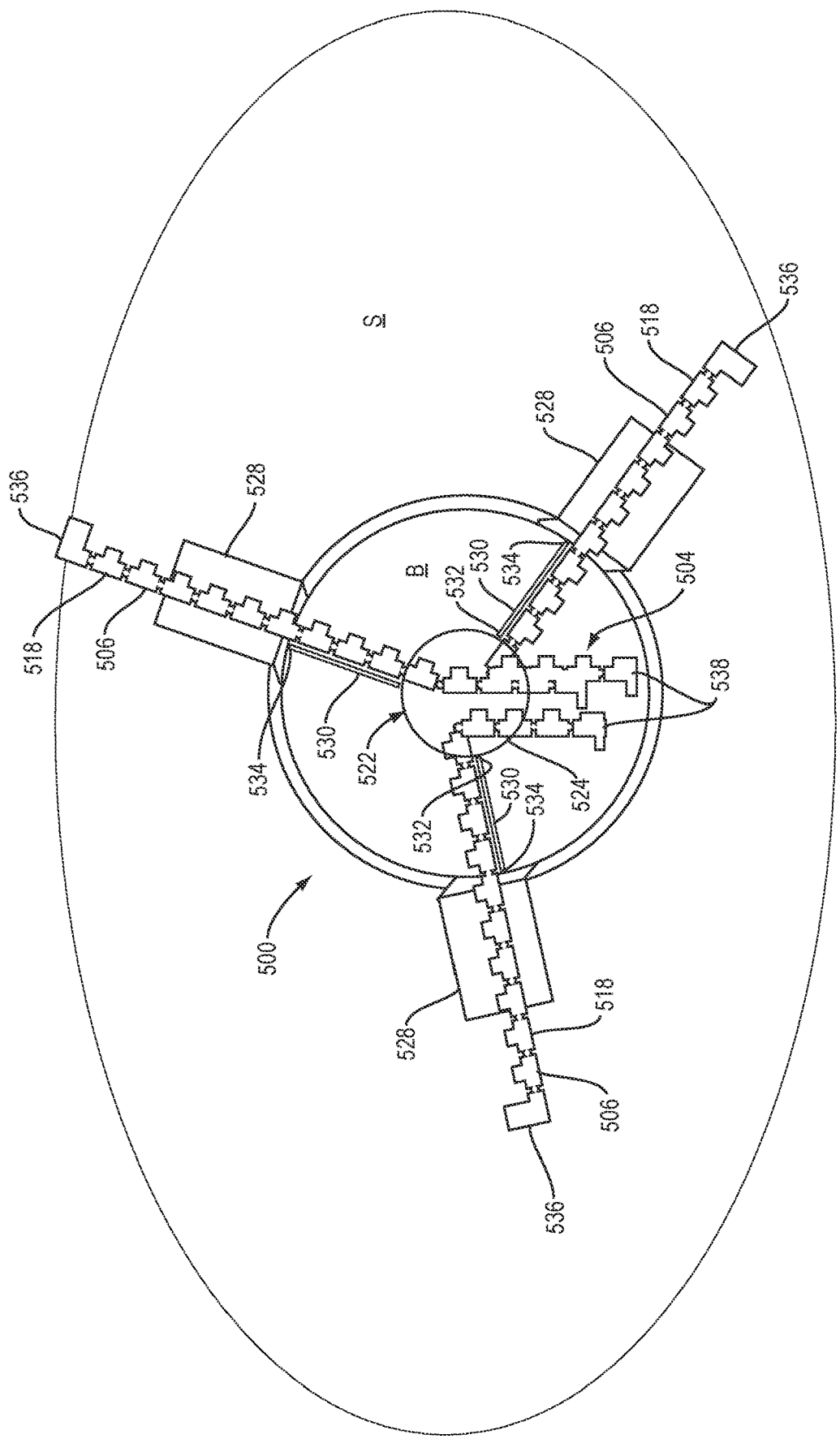
FIG. 15 is another environmental, schematic view of an exemplary coupled annulus and catheter system for placement of biocompatible electrodes and like devices according to the present invention, as used in a patient's skull.

FIGS. 9, 10A, 10B, 10C, 10D, 10E and 11 illustrate exemplary catheters 502 of a system 500 for placement of biocompatible electrodes (the complete system 500 being shown in FIGS. 14 and 15). The catheter 502 includes a cylindrical guide tube 504, the guide tube 504 having a longitudinal axis L and three guide elements 506 extending along (i.e., so as to surround and be generally parallel with) the longitudinal axis L (see FIG. 10A). In other embodiments, the guide tube 504 has more than three guide elements 506 (e.g., four, five or six guide elements). The guide elements 506 are curved and thereby configured to fit together and collectively form a continuous lumen 507, or bore hole, through the catheter 502. The lumen 507 extends along the longitudinal axis L of the guide tube 504 and is dimensioned to receive a DBS electrode or similar device therein.

The catheter 502 (i.e., its cylindrical guide tube 504), is splittable, such that the guide elements 506 may be easily separated from each other by a surgeon or other operator to facilitate the catheter's safe and effective removal from a burr hole or other opening, as further discussed below.

The guide elements 506 are constructed of a biocompatible material, such as steel or a biocompatible metal alloy.

Figure 9:
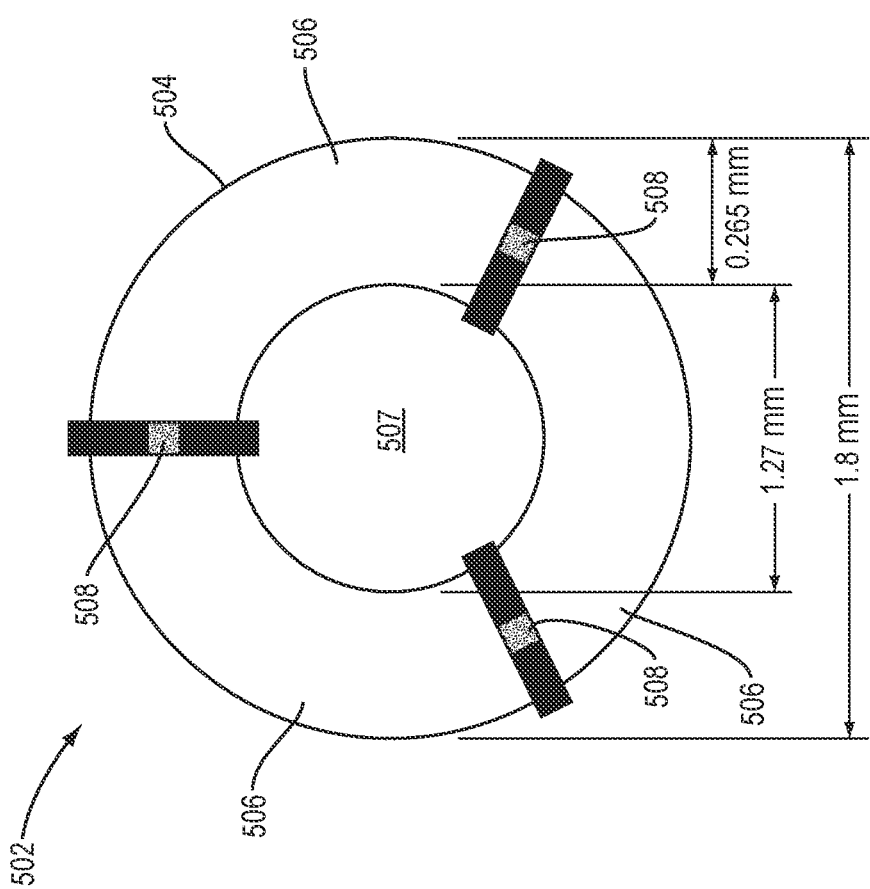
FIG. 9 is a top, schematic view of a catheter of an exemplary coupled annulus and catheter system according to the present invention.

As shown in FIGS. 9, 10D and 10E, magnetic connectors 508 oriented longitudinally along the bodies of each guide element 506 may be used to removably connect the guide elements 506 to each other to form the cylindrically shaped guide tube 504. Alternatively, other types of connectors may be used to removably connect the guide elements 506 to each other.

Each of the guide elements 506 includes first and a second ends 510, 512 proximate the respective opposed ends of the longitudinal axis L of the guide tube 504, as shown in FIG. 10A.

Figure 11:
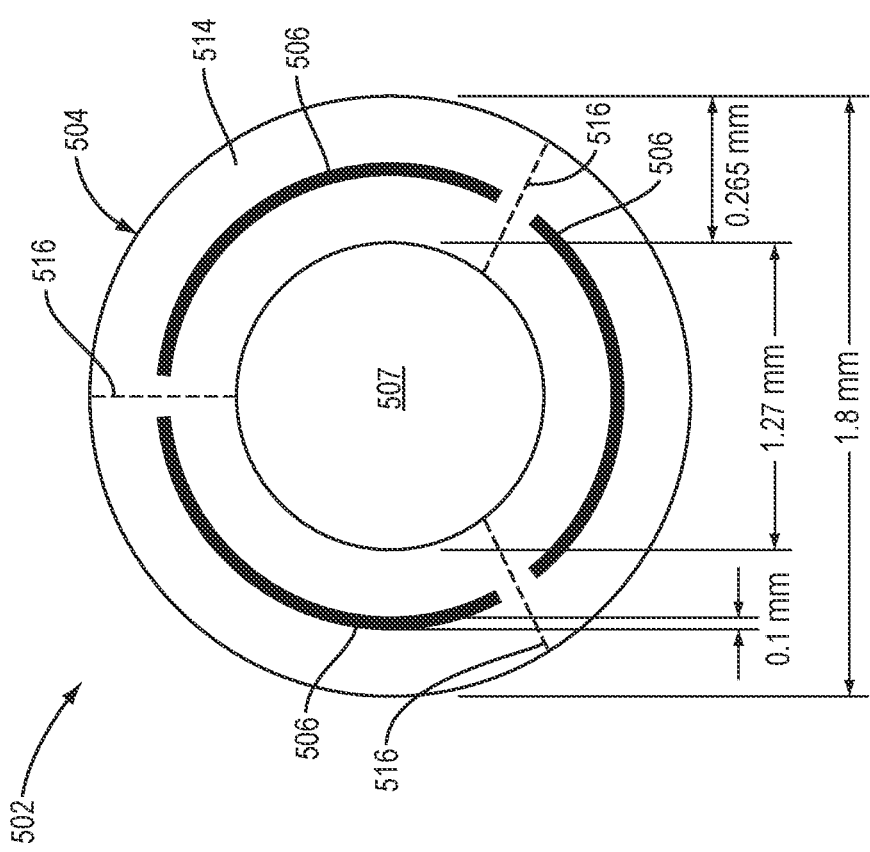
FIG. 11 is a top, schematic view of another catheter of an exemplary coupled annulus and catheter system according to the present invention.

In various embodiments, the catheter 502 includes a deformable silicone rubber sheath 514 that encases the guide tube 504 and its guide elements 506 (see FIG. 11). In some embodiments, the silicone sheath 514 has a plurality of perforations 516 formed along its length (i.e., extending along/parallel to longitudinal axis L of the guide tube 504/catheter 502), as shown in FIG. 11. The perforations 516 are the same as, or similar to, the perforations formed in the silicone sheaths of the embodiments illustrated in FIGS. 3A, 3B, 3C, 3E and 4, wherein these perforations enable a surgeon or other operator to separate portions of the silicone sheath 514 and remove them from the guide tube 504, as shown in FIG. 3E. The silicone sheath 514 can also include pull flaps (see FIG. 3B), lips (see FIGS. 10B and 10E, discussed below) or other means to facilitate separating the perforated portions of the silicone sheath 514.

In other embodiments, the catheter 502 is provided without the silicone sheath.

In an embodiment, each of the guide elements 506 includes a plurality of rotatably-connected segments 518 that collectively extend between the first and second ends 510, 512 (see FIGS. 14-17). The rotatably-connected segments 518 are each connected to the adjacent segment(s) by a joint 520 and provide each guide element 506 with degrees of rigidity and flexibility, so that each guide element 506 can be rotated between separated and united/cylindrical configurations during the operation of the system 500, as further described below.

Figure 12:
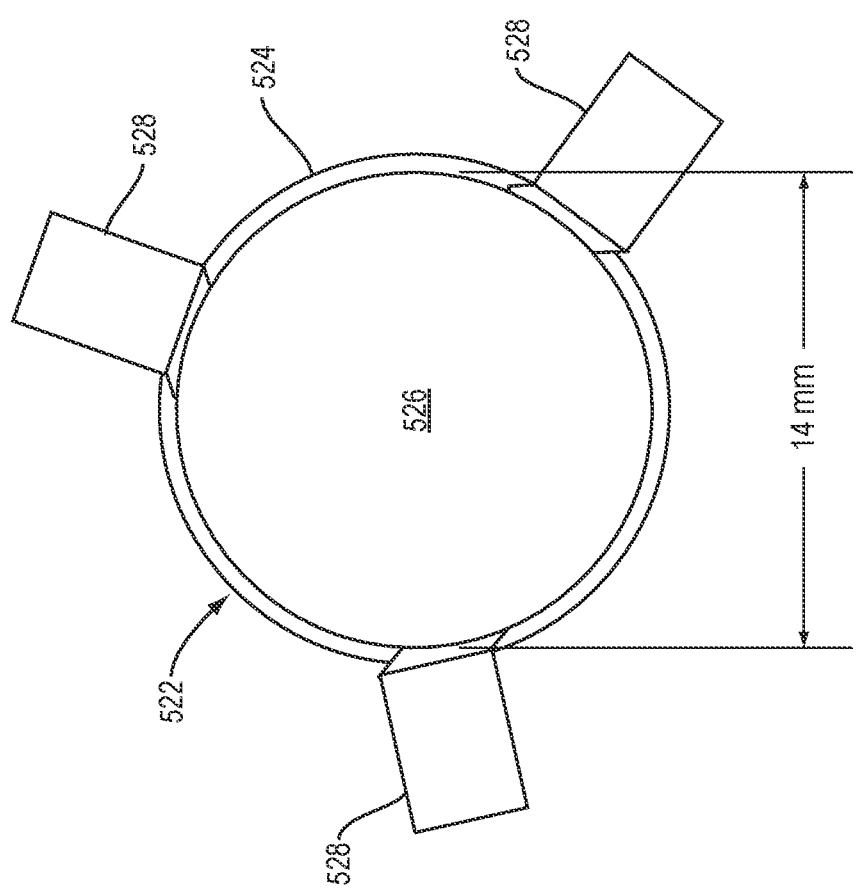
FIG. 12 is a top, schematic view of an annulus of an exemplary coupled annulus and catheter system according to the present invention.
Figure 13:
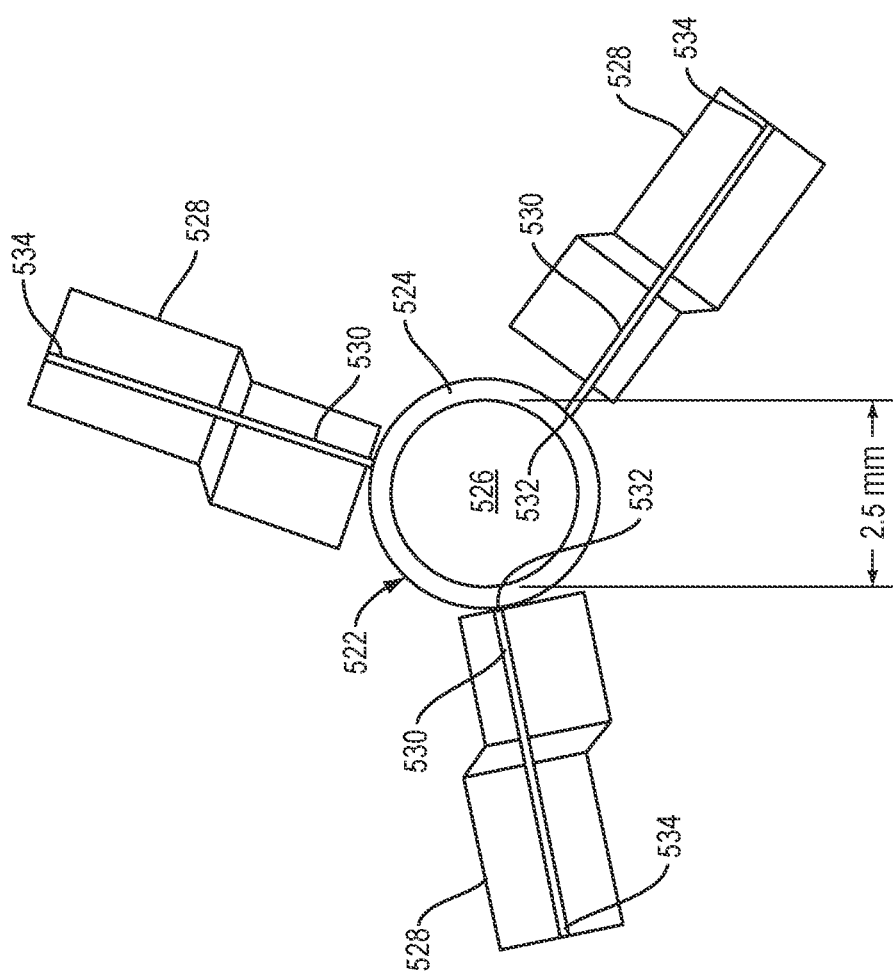
FIG. 13 is a top, schematic view of another annulus of an exemplary coupled annulus and catheter system according to the present invention.

FIGS. 12 and 13 illustrate an exemplary annulus 522 of the system 500. The annulus 522 is configured such that it is flush, or nearly flush, with a surface surrounding an opening (e.g., a burr hole) created in a surface of the patient's body (e.g., the patient's skull, or other bony surface), such that there is no protruding component, or no significant protruding component, of the annulus 522 above the surface in which the burr hole is made. This configuration provides a mounted insertion platform for mechanically and precisely controlling the stereotactic placement of DBS electrodes, or similar devices, in the patient's body, and thereby enables superior accuracy via computer automation of the insertion process, compared to manual insertion. Such accuracy is an absolute necessity during procedures involving the stereotactic placement of DBS electrodes, or similar devices. As such, the use of the coupled annulus-catheter system 500 enables the manipulation of the catheter device to be potentially integrated into said stereotactic placement system, providing an option where manual user control is unnecessary.

With continued reference to FIGS. 12 and 13, the annulus 522 includes a circumferential rim 524 defining an interior circular space 526 that is dimensioned to receive the catheter 502 therethrough, and a number of legs 528 engaging the rim 524 and extending outwardly therefrom. In various embodiments, the rim 524 and legs 528 are formed from biocompatible metal wire or other thin biocompatible metal materials.

In the embodiment illustrated in the figures, the annulus 522 has three legs 528. In other embodiments, the annulus 522 has fewer legs 528 (e.g., one or two legs) or more than three legs 528 (e.g., four, five or six guide legs). In various embodiments, each of the legs 528 has an "L" shape, an "S" shape (i.e., an "L" shape with an additional horizontal portion), or a "U" shape in which the "sides" of the "U" fit above and below the incised bone (such that one is flush with the bone intracranially and the other is flush with the bone extracranially) bridged by the bottom of the "U" which is flush to the wall of the bony craniotomy or burr hole.

As illustrated in FIGS. 14 and 15, the legs 528 are configured to securely fit into an opening in a patient's body part, such as a burr hole B formed in the surface of a patient's skull S. More particularly, a first portion of each of the legs 528 insertably engages the burr hole B, and a second portion of each of the legs 528 engages the skull surface S surrounding the burr hole B (i.e., around the edge of the burr hole B circumferentially).

In various embodiments, the legs 528 include one or more eyelets (not shown) that are configured to receive a screw or another type of fastener for fixing the leg 528 rigidly to the skull S. In other embodiments, the legs 528 are configured to fasten to the skull surface S without a screw or fastener. For example, the legs 528 may fit perfectly, given a prescribed size of the drilled or cut hole in the bone, such that it is axially fixed (i.e., the annulus 522 as a whole, has a fixed diameter, and therefore the U, L, or S-shaped legs 528 alone sufficiently hold in place the suspended or non-suspended rim 524, depending on whether legs are implemented). In another example, the legs 528 and rim 524 themselves have a telescoping structure such that their exact diameter can be adjusted. In this way, an annulus 522 that is initially smaller than the diameter of the burr hole B could be fit into place at the edges of the burr hole B without requiring the use of a fastening screw, if the legs 528 fit snugly.

With further reference to FIGS. 12-15, the rim 524 and interior circular space 526 of the annulus 522 are configured to be placed in the geometrical center of the burr hole B. The maximum diameter of the rim 524 is the same as the diameter of the burr hole B.

In some embodiments, the rim 524 rests on the circumference/edge of the burr hole B when the annulus 522 is placed during surgery on a patient. In some embodiments, the annulus 522 further includes a number of rods 530 (see FIGS. 13 and 15). In various embodiments, the rods 530 are formed from biocompatible metal wire or other thin biocompatible metal materials. The number of rods 530 is the same as the number of legs 528, so, in various embodiments, the annulus may have one, two, three, four, five or other numbers of rods 530 and legs 528. As shown in FIGS. 13 and 15, each of the rods 530 has a first end 532 connected to the rim 524 of the annulus 522 and a second end 534 connected to a corresponding one of the legs 528. This configuration facilitates the suspension of the rim 524 of the annulus 522 within the burr hole B via the rods 530 that extend from the rim 524 outwardly to the legs 528 (i.e., by a surgeon or other user, or the stereotactic placement system itself, to which the annulus-catheter system 500 may be mechanically coupled, and by which it may be controlled, as shown in FIG. 15. In one embodiment, the rim 524 is configured to have a variable diameter and is moveable between the first and second ends 532, 534 of the rods 530, with a predetermined minimum diameter at or near the center of the burr hole B, as shown in FIG. 15. On the other hand, the rim 524 of the annulus 522 shown in FIG. 14 is positioned so that it has a predetermined maximum diameter (rods not shown). In various embodiments, the minimum diameter of the rim 524 includes 2.5 mm, while its maximum diameter includes 14 mm. In other embodiments, such as when the annulus 522 is used in a larger craniotomy hole rather than a burr hole, the rim has a maximum diameter of 8 cm. Other medical applications of the system 500 and their correspondingly sized openings in a patient's body part will dictate other exemplary diameters of the rim 524.

Figure 17:
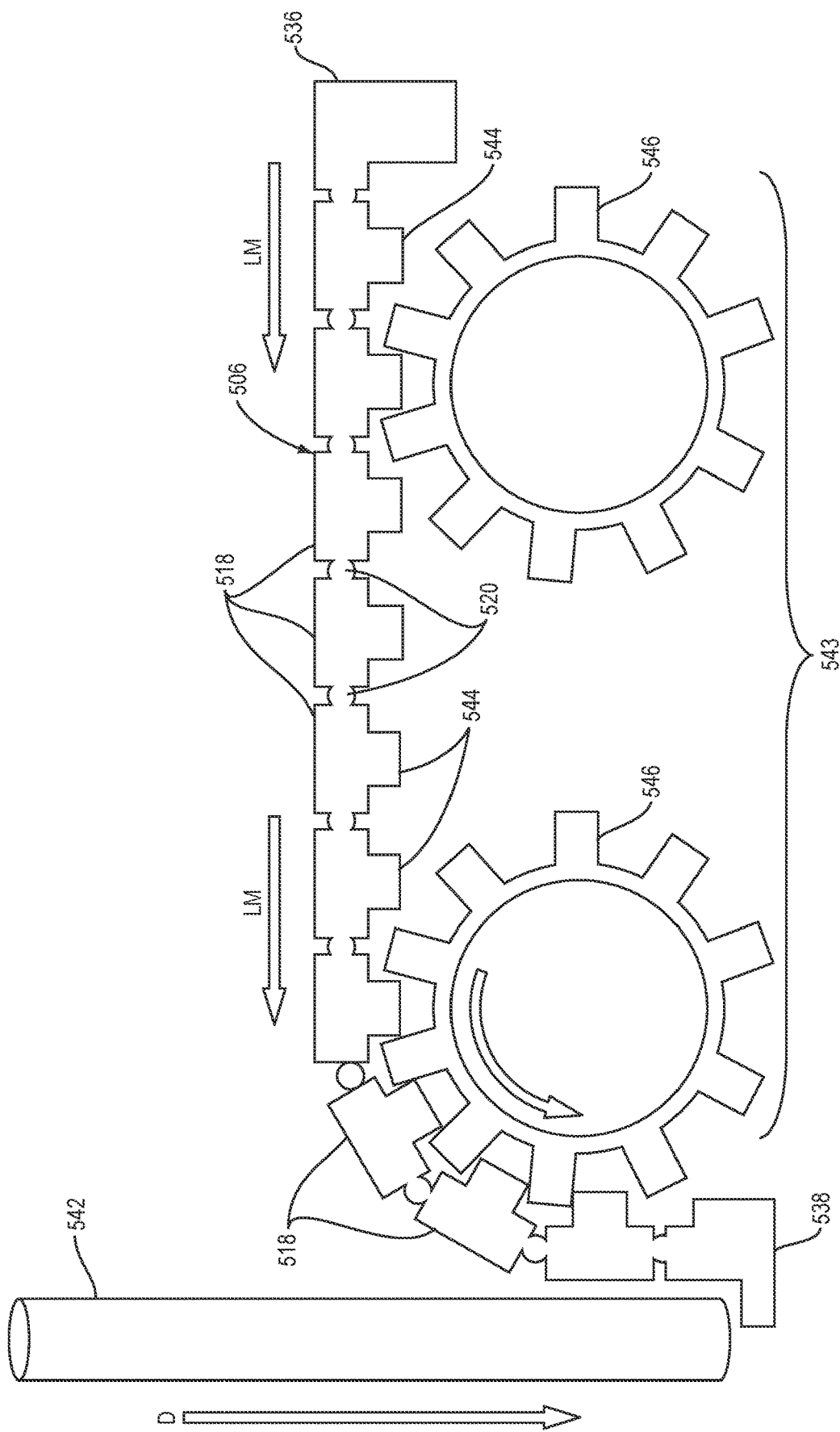
FIG. 17 further illustrates components of the coupled annulus and catheter system shown in FIGS. 14 and 15.

In various embodiments of the coupled system 500, the guide elements 506 of the catheter 502 are connected to a portion of the annulus 522 (i.e., the legs 528 and/or the rim 524 and/or the rods 530 thereof). Such attachment may be accomplished via a track mechanism ("tracks") such that the lateral degree of motion of the guide elements 506 may be limited, and such that the axial movement (i.e., movement into and out of the burr hole B (as opposed to 'lateral movement' which refers to movement within, for example, the plane of insertion)) of the guide elements 506 with respect to the burr hole B may be carefully controlled. In different embodiments, the track mechanism is separable or inseparable to the annulus 522, i.e., the legs 528, and along which the guide elements 506 will engage as they move into or out of the burr hole B. One embodiment of the track mechanism 543 is shown in FIG. 17 and further discussed below. Such a track mechanism may incorporate a series of motors which may enable a computer-driven stereotactic insertion system optimized for insertion of DBS catheters and electrodes to exert exquisitely precise control over the insertion and removal of the catheter 502 about the rim 524 of the annulus 522.

In various embodiments, the electrode insertion/placement and catheter insertion/removal operations of the system of the present invention may be fully automated, to avoid any human error from manually-controlled insertion/placement/removal operations. In some such embodiments, this is achieved via the use of a computer-driven stereotactic insertion system optimized for insertion of DBS catheters and electrodes.

Referring now to FIGS. 10B, 10C, 10D, 10E and 14-17, in an embodiment, the guide elements 506 comprising the guide tube 504 of the catheter 502 each have a first, or proximal, lip (or flap) 536 disposed at the first end 510 of the guide tube 504 (i.e., proximal from the point of implantation into the patient—the trailing portion of the catheter 502/ guide tube 504 that protrudes from the burr hole B). Each guide element 506 also has a second, or distal, lip 538 disposed at the second end 512 of the guide tube 504 (i.e., the distal, or leading implanted end of the catheter 502/guide tube 504 that is inserted through the annulus 522 into the burr hole B), on the opposite end of the guide element 506 as the proximal lip 536. The proximal and distal lips 536, 538 are configured to be oriented perpendicularly to longitudinal axes of the guide elements 506 and the longitudinal axis L of the guide tube 504. The proximal lips 536 of the respective guide elements 506 are configured to interlock or adhere with each other together (for example, by magnetic connectors similar to magnetic connectors 508) to form a proximal circular rim 540 at the first end 510 of the guide tube 504 (see FIGS. 10A and 10B). In some embodiments, each of the proximal lips 536 includes a protrusion 537, and all of the respective protrusions 537 extend beyond the respective first ends 510 of the guide elements 506 that form the proximal circular rim 540 of the assembled tube guide 504, and the protrusions 537 fit together in a circular configuration (see FIG. 10B). Similarly, the distal lips 538 of the respective guide elements 506 are configured to interlock with each other together to form another, distal circular rim 541 at the second end 512 of the guide tube 504. In some embodiments, each of the distal lips 538 includes a protrusion 539, and all of the respective protrusions 539 extend beyond the respective second ends 512 of the guide elements 506 that form the distal circular rim 541 of the assembled tube guide 504, and the protrusions 539 fit together in a circular configuration (see FIGS. 10C and 10D). The circular rims 540, 541 formed by the proximal and distal lips 536, 538 at the first and second ends 510, 512 define the electrode-receiving lumen 507 that extends between them (see FIGS. 10A, 10D and 10E). In another embodiment, the proximal end protrusions 539 protruding from each guide element 506 each form a non-circular flap such that it can be easily pulled by the surgeon or other user, as in FIG. 3B.

Figure 16:
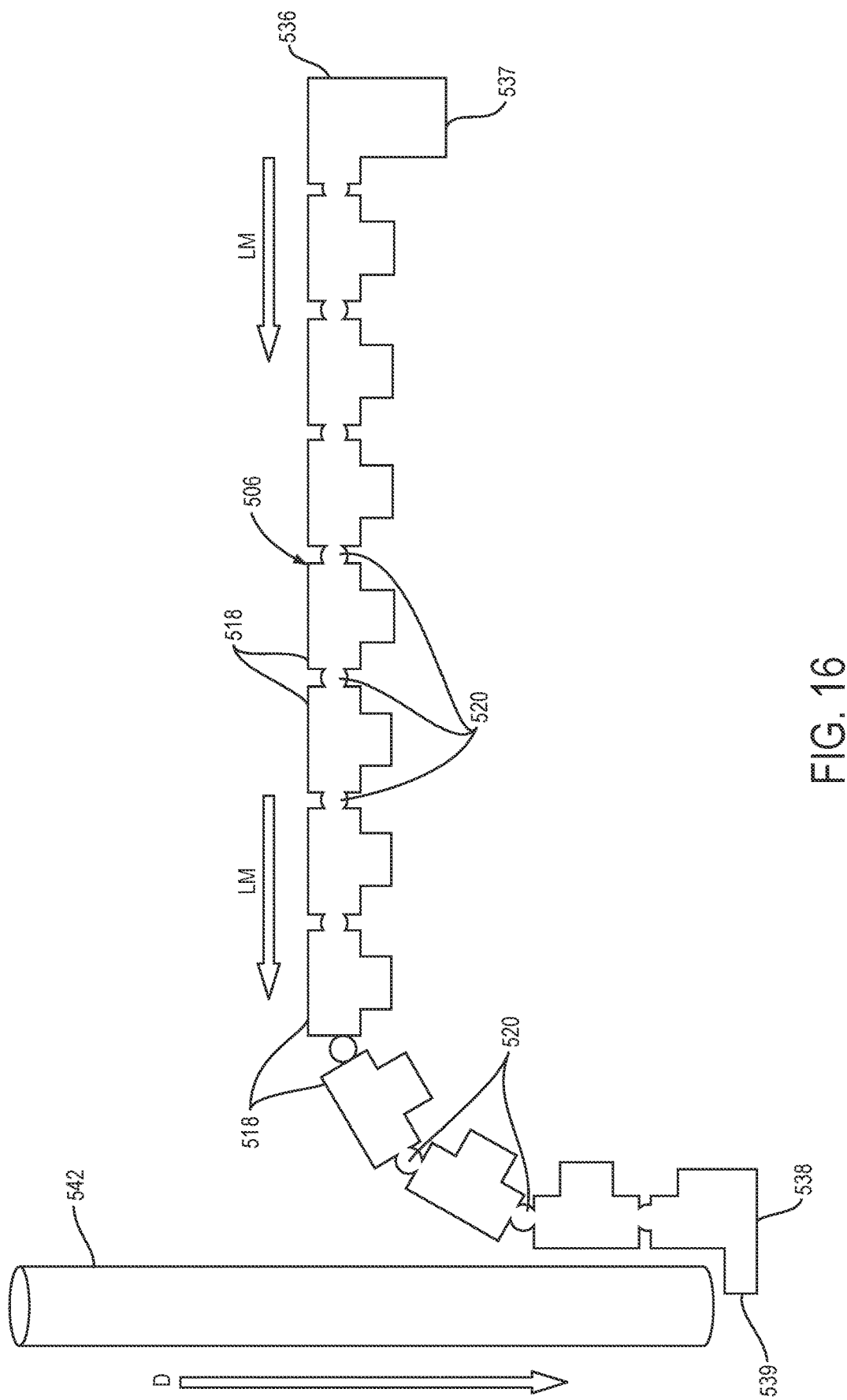
FIG. 16 illustrates components of the coupled annulus and catheter system shown in FIGS. 14 and 15.

The proximal and distal lips 536, 538 of the guide elements 506 provide structural and functional advantages to the system 500. As shown in FIGS. 16 and 17, the distal lips 538 form the distal circular rim 541, and thereby provide a surface upon which a rigid stylet 542 (used in the insertion of DBS electrodes or similar devices) is received to urge the guide elements 506 in a distal direction (see arrow D) in a process to insert the catheter 502 into the burr hole B. In an embodiment, the guide tube 504 of the catheter 502 is separated into the guide elements 506 (see FIGS. 14 and 15) at the start of the insertion procedure, wherein the distal motion of the stylet 542 pushes the distal lips 538 of the separated guide elements distally, causing sequential rotation of the guide elements 506 (i.e., rotation towards the stylet 542, and each other, via the joints 520 between the rotatably-connected segments 518) so that the guide elements 506 ultimately unite to form the guide tube 504 and have a cylindrical configuration (see FIG. 10A, and similar cylindrical configurations of the embodiments of FIGS. 1-8). In other embodiments, the system 500 is computer-controlled and motor driven, so that the action of a stylet 542 is not required for rotating the guide elements 506. Further, once the guide elements 506 converge to form the cylindrical guide tube 504, the proximal lips 536 of the respective guide elements 506 (e.g., the protrusions 537) converge to form the proximal circular rim 540, as described above and shown in FIGS. 10A-10E. The proximal circular rim 540 protrudes from the burr hole B and constitutes a means of applying manual force (in an embodiment where manual force is used to separate the guide elements 506 from each other). More particularly, force is applied in order to drive the distal lip 538, which unlike the proximal lip 536 (which is oriented concentrically outside of the guide tube 504), protrudes concentrically inside of the guide tube 504 (i.e., within the lumen 507) by the stylet 542 which occupies the interior of the guide tube 504 but abuts the distal lip 538 during insertion into the burr hole B (or other opening) in order to push the guide tube 504 to descend to its position within, for example, deep brain structures. The stylet 542 is then withdrawn, without meeting resistance, while the guide tube 504 has now been placed at its target within the tissue. An electrode which is thinner than the stylet 542 may then be inserted without catching on the distal lip 538 (see FIGS. 10C and 10D), and does not fill the entire bottom surface of the guide tube 504, leaving a bore smaller in diameter than the inner diameter of the lumen 507 of the guide tube 504.

In some embodiments, the system 500 also includes tracks as part of a track mechanism, as discussed above. The track mechanism may be used to operably couple the guide elements 506 of the catheter 502 to a portion of the annulus 522 (i.e., the legs 528, the rim 524, the rods 530 or two or all thereof). An embodiment of the track mechanism 543 is shown in FIG. 17, and is configured to enable and limit the lateral motion (arrow LM) of the guide elements 506, and such that the axial movement of the guide elements 506 with respect to the burr hole B may be carefully controlled, including by the system used otherwise for stereotactic placement of electrodes or other like devices into deep brain structures or other tissues.

The track system 543 of FIG. 17 includes cooperating components, namely, teeth 544 protruding from each of the rotatably-connected segments 518 of the guide elements 506, and the teeth of one or more gears 546 positioned so as to operably engage the teeth 544 of the segments 518, and control movement of the guide elements 506 in a lateral and distal direction (see arrow LM). In one embodiment, the gear(s) 546 may prevent rotation in one direction (e.g., clockwise) until a latch (not shown) is removed. Further, the proximal lip 536 of each guide element 506 is sized to lock the guide element 506 and guide tube 504 in place, ensuring that it does not move past the gear 546 (see FIG. 17). In another embodiment, the gears may themselves permit bi-directional (i.e., clockwise or counterclockwise) rotation but would be coupled to motors within or around the track and precisely controlled by the stereotactic insertion system.

Further, the operation of the coupled annulus described herein may be incorporated mechanically into a system already used for inserting the catheter as part of commercially available DBS systems by means of a gear system being built into the tracks described above, such that the same system used for stereotactic insertion of the catheter and electrode at the proper location and trajectory into the underlying tissues may also be used to withdraw the catheter safely from the underlying tissues, and in a controlled manner. In this contingency, the tube would consist only of the steel (or other similar biocompatible metal alloy) components, without the silicone outer casing, and could be cleansed and re-used for multiple patient along with the rest of the system.

In other embodiments, the guide elements 506 of the catheter 502 may be secured to the annulus 522 (including any of its components, such as the leg(s) 528, rod(s) 530, or rim 522) by some other means of coupling, such as by incorporating a track or rail system into any of these components into which the guide elements 506 of the catheter 502 slide smoothly between the system's two configurations, namely, (1) a united cylindrical configuration with the catheter guide tube 504 having fully interconnected guide elements 506, and (2) a separated configuration with the guide elements 506 at least partially disengaged from each other, so as to facilitate the safe and effective removal of the catheter 502/guide tube 504/guide elements 506 from the burr hole B or other opening.

In various other embodiments, the geometry of the system 500, including the annulus 522, may be scaled up by an order of magnitude such that it can be applied to a circular craniotomy, rather than a burr hole (which is significantly smaller), for application of other similar devices which must be inserted under similar constraints. In some such embodiments, the catheter 502 coupled to the annulus 522 is also scaled up, while in others the catheter 502 is not scaled up.

In various embodiments, the dimensions of the catheter, annulus and other components of the system 500 are the same as those of the embodiments described and shown in FIGS. 3A-8B. Dimensions of the catheter, annulus and other components may vary depending on individual use cases, for example based on the particular mechanical components applied to aid in automatic function. The dimensions identified in the various figures are exemplary, and should not be construed as limiting. Further, the catheter and other system components may be upscaled for use in other non-DBS applications, such as the insertion of a precisely targeted stimulation or drug delivery device through a craniotomy, rather than through a burr hole, as described in the preceding paragraph.

The foregoing description of the preferred embodiments of the invention is by way of example only, and other variations of the above-described embodiments and methods are provided by the present invention. The embodiments described herein have been presented for purposes of illustration and are not intended to be exhaustive or limiting. Many variations and modifications are possible in light of the foregoing teaching. The invention is limited only by the following claims.

We claim:

1. A system for placement of biocompatible electrodes in an opening formed in a patient's body part, comprising:
    a catheter including a guide tube, the guide tube having a longitudinal axis and at least three guide elements extending along the longitudinal axis;
        each of the guide elements including a first end, a second end, a plurality of rotatably-connected segments extending between the first and second ends, and a plurality of joints connecting adjacent ones of the segments;
        the guide elements being configured to releasably fit together and collectively form a continuous lumen through the catheter, the lumen extending along the longitudinal axis of the guide tube and being dimensioned to receive an electrode therein;
    an annulus including a circumferential rim defining an interior circular space that is dimensioned to receive the catheter therethrough, and a number of legs engaging the rim and extending outwardly therefrom, the annulus being configured to be secured in the opening;
    and means for operably coupling the catheter to the annulus.

2. The system of claim 1, wherein the catheter is moveable between a first, united cylindrical configuration with each one of the guide elements of the guide tube being fully interconnected to the others of the guide elements, and a second, separated configuration with the guide elements being at least partially disengaged from each other.

3. The system of claim 2, wherein the catheter further comprises a silicone sheath in which the guide elements are enclosed, the silicone sheath including perforations extending along the longitudinal axis, whereby the silicone sheath is peelable away from the guide elements when the catheter is moved from its united cylindrical configuration to its separated configuration.

4. The system of claim 2, wherein the catheter further comprises three magnetic connectors, wherein the guide elements are made of a magnetic material, and wherein each of the magnetic connectors is placed between two adjacent guide elements to removably connect the guide elements to each other to form the cylindrically shaped guide tube when the catheter is in its united cylindrical configuration.

5. The system of claim 1, wherein each of the guide elements includes a proximal lip disposed at the first end of the guide tube, and a distal lip disposed at the second end of the guide tube, on an opposite end of the guide element as the proximal lip;
    wherein the proximal lips of the respective guide elements are configured to interlock with each other to form a proximal circular rim at the first end of the guide tube when the catheter is in its united cylindrical configuration; and
    wherein the distal lips of the respective guide elements are configured to interlock with each other to form a distal circular rim at the second end of the guide tube; and
    wherein the proximal and distal circular rims formed by the proximal and distal lips, define the lumen between the proximal and distal circular rims.

6. The system of claim 1, wherein the rim of the annulus is configured to be placed in a geometrical center of the opening formed in the patient's body part.

7. The system of claim 6, wherein the annulus further includes a number of rods that is the same as the number of legs, such that there is a one-to-one correspondence between the rods and legs, each of the rods having a first end connected to the rim of the annulus and a second end connected to a corresponding one of the legs, and whereby the rods facilitate suspension of the rim of the annulus within the opening formed in the patient's body part.

8. The system of claim 6, wherein the rim is configured to have a variable diameter.

9. The system of claim 2, wherein the coupling means includes a track mechanism connected to the annulus, the track mechanism including at least one toothed gear, and teeth protruding from each of the rotatably-connected segments of the guide elements and configured to operably engage teeth of the at least one toothed gear, whereby lateral movement of the guide elements is limited by the at least one toothed gear, and axial movement into and out of the opening formed in a patient's body part is carefully controlled.

10. The system of claim 9, wherein the track mechanism is operably connected to the legs and/or the rim of the annulus.

11. The system of claim 1, wherein the electrode is a DBS electrode, the patient's body part is a skull, and the opening formed therein is selected from the group consisting of a burr hole and a craniotomy hole.

12. A system for placement of DBS electrodes in an opening formed in a patient's skull, comprising:
    a catheter including a guide tube, the guide tube having a longitudinal axis and at least three guide elements extending along the longitudinal axis;
        each of the guide elements including a first end, a second end, a plurality of rotatably-connected segments extending between the first and second ends, and a plurality of joints connecting adjacent ones of the segments;
        the guide elements being configured to releasably fit together and collectively form a continuous lumen through the catheter, the lumen extending along the longitudinal axis of the guide tube and being dimensioned to receive a DBS electrode therein;
        the catheter being moveable between a first, united cylindrical configuration with each one of the guide elements of the guide tube being fully interconnected to the others of the guide elements, and a second, separated configuration with the guide elements being at least partially disengaged from each other;
    an annulus including a circumferential rim defining an interior circular space that is dimensioned to receive the catheter therethrough and a number of legs engaging the rim and extending outwardly therefrom, the annulus being configured to be secured in the skull opening; and
    a track mechanism connected to the annulus, the track mechanism including at least one toothed gear, and teeth protruding from each of the rotatably-connected segments of the guide elements and configured to operably engage teeth of the at least one toothed gear, whereby the annulus and catheter are operably coupled to each other, whereby lateral movement of the guide elements is limited by the at least one toothed gear, and axial movement into and out of the skull opening is carefully controlled.

13. The system of claim 12, wherein the annulus further includes a number of rods that is the same as the number of legs, such that there is a one-to-one correspondence between the rods and legs, each of the rods having a first end connected to the rim of the annulus and a second end connected to a corresponding one of the legs, and whereby the rods facilitate suspension of the rim of the annulus within the skull opening.

14. The system of claim 13, wherein the track mechanism is connected to one or more of the legs, rim and rods of the annulus.

15. The system of claim 12, wherein each of the guide elements includes a proximal lip disposed at the first end of the guide tube, and a distal lip disposed at the second end of the guide tube, on an opposite end of the guide element as the proximal lip;
- wherein the proximal lips of the respective guide elements are configured to interlock with each other to form a proximal circular rim at the first end of the guide tube when the catheter is in its united cylindrical configuration; and
- wherein the distal lips of the respective guide elements are configured to interlock with each other to form a distal circular rim at the second end of the guide tube;
- the proximal and distal circular rims formed by the proximal and distal lips define the lumen between the proximal and distal circular rims.

16. The system of claim 15, wherein the distal circular rim is dimensioned to receive a rigid stylet that is configured to urge the guide elements in a distal direction for facilitating insertion of the catheter into the skull opening.

17. The system of claim 15, wherein the proximal circular rim is configured to protrude from the skull opening and constitute a means of applying manual force to the stylet in order to position the guide tube and catheter in the patient's skull opening.

18. A kit for the placement of DBS electrodes into an opening in a patient's skull, comprising:
- a catheter including a guide tube, the guide tube having a longitudinal axis and at least three guide elements extending along the longitudinal axis;
- each of the guide elements including a first end, a second end, a plurality of rotatably-connected segments extending between the first and second ends, and joints connecting adjacent ones of the segments;
- the guide elements being configured to releasably fit together and collectively form a continuous lumen through the catheter, the lumen extending along the longitudinal axis of the guide tube and being dimensioned to receive a DBS electrode therein;
- the catheter being moveable between a first, united cylindrical configuration with each one of the guide elements of the guide tube being fully interconnected to the others of the guide elements, and a second, separated configuration with the guide elements being at least partially disengaged from each other;
- an annulus including a circumferential rim defining an interior circular space that is dimensioned to receive the catheter therethrough and a number of legs engaging the rim and extending outwardly therefrom, the annulus being configured to be secured in the skull opening;
- a track mechanism connected to the annulus, the track mechanism including at least one toothed gear, and teeth protruding from each of the rotatably-connected segments of the guide elements and configured to operably engage teeth of the at least one toothed gear, whereby the annulus and catheter are operably coupled to each other; and
- a stylet that is configured to urge the guide elements in a distal direction for facilitating insertion of the catheter into the skull opening.

* * * * *